US008303956B2

(12) United States Patent
Sällberg et al.

(10) Patent No.: US 8,303,956 B2
(45) Date of Patent: *Nov. 6, 2012

(54) GLYCOSYLATED SPECIFICITY EXCHANGERS

(75) Inventors: Matti Sällberg, Stockholm (SE); Anders Vahlne, Stockholm (SE); Maria Perdomo, Solna (SE)

(73) Assignee: Chrontech Pharma AB, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/748,151

(22) Filed: Mar. 26, 2010

(65) Prior Publication Data

US 2010/0183635 A1  Jul. 22, 2010

Related U.S. Application Data

(63) Continuation of application No. 11/930,860, filed on Oct. 31, 2007, now abandoned, which is a continuation of application No. 10/773,628, filed on Feb. 5, 2004, now Pat. No. 7,318,926.

(60) Provisional application No. 60/446,172, filed on Feb. 6, 2003.

(51) Int. Cl.

| A61K 39/00 | (2006.01) |
|---|---|
| C07K 16/00 | (2006.01) |
| C07K 1/00 | (2006.01) |
| C07K 14/00 | (2006.01) |
| C07K 17/00 | (2006.01) |
| C12P 21/08 | (2006.01) |

(52) U.S. Cl. ............... 424/178.1; 530/387.1; 530/388.8; 530/389.7; 530/391.5; 530/391.7; 530/395

(58) Field of Classification Search ........................ None
See application file for complete search history.

(56) References Cited

U.S. PATENT DOCUMENTS

| 4,169,138 A | 9/1979 | Jonsson |
| 4,376,110 A | 3/1983 | David et al. |
| 4,471,058 A | 9/1984 | Smith et al. |
| 4,486,530 A | 12/1984 | David et al. |
| 4,589,881 A | 5/1986 | Pierschbacher et al. |
| 4,946,778 A | 8/1990 | Ladner et al. |
| 5,091,513 A | 2/1992 | Huston et al. |
| 5,175,096 A | 12/1992 | Hook et al. |
| 5,189,015 A | 2/1993 | Hook et al. |
| 5,196,510 A | 3/1993 | Rodwell et al. |
| 5,260,189 A | 11/1993 | Formoso et al. |
| 5,320,951 A | 6/1994 | Hook et al. |
| 5,416,021 A | 5/1995 | Hook et al. |
| 5,440,014 A | 8/1995 | Hook et al. |
| 5,561,049 A | 10/1996 | Vold et al. |
| 5,571,511 A | 11/1996 | Fischer |
| 5,571,514 A | 11/1996 | Hook et al. |
| 5,582,975 A | 12/1996 | Milliman |
| 5,583,042 A | 12/1996 | Roth |
| 5,601,830 A | 2/1997 | Su et al. |
| 5,627,263 A | 5/1997 | Ruoslahti et al. |
| 5,652,217 A | 7/1997 | Hook et al. |
| 5,700,928 A | 12/1997 | Hodgson et al. |
| 5,714,332 A | 2/1998 | Lussow et al. |
| 5,766,591 A | 6/1998 | Brooks et al. |
| 5,766,857 A | 6/1998 | Ruoslahti et al. |
| 5,770,208 A | 6/1998 | Fattom et al. |
| 5,770,702 A | 6/1998 | Hook et al. |
| 5,776,712 A | 7/1998 | Kuusela et al. |
| 5,789,549 A | 8/1998 | Hook et al. |
| 5,840,846 A | 11/1998 | Hook et al. |
| 5,843,774 A | 12/1998 | Ginsberg |
| 5,846,536 A | 12/1998 | Bissell et al. |
| 5,866,541 A | 2/1999 | Hook et al. |
| 5,869,232 A | 2/1999 | Sällberg |
| 5,888,738 A | 3/1999 | Hendry |
| 5,922,548 A | 7/1999 | Lussow et al. |
| 5,929,220 A | 7/1999 | Tong et al. |
| 5,939,273 A | 8/1999 | Lussow et al. |
| 5,942,606 A | 8/1999 | Lal et al. |
| 5,955,078 A | 9/1999 | Burnham et al. |
| 5,980,908 A | 11/1999 | Hook et al. |
| 5,981,274 A | 11/1999 | Tyrrell et al. |
| 6,008,341 A | 12/1999 | Foster et al. |
| 6,030,613 A | 2/2000 | Blumberg et al. |
| 6,040,137 A | 3/2000 | Sälberg |
| 6,046,040 A | 4/2000 | Nishiguchi et al. |
| 6,066,648 A | 5/2000 | Duggan et al. |
| 6,077,677 A | 6/2000 | Hodgson et al. |
| 6,086,875 A | 7/2000 | Blumberg et al. |
| 6,086,895 A | 7/2000 | Hook et al. |
| 6,087,330 A | 7/2000 | Kogan et al. |

(Continued)

FOREIGN PATENT DOCUMENTS

EP      0 182 546      5/1986

(Continued)

OTHER PUBLICATIONS

Li et al. Bacteria Targeted by Human Natural Antibodies Using alpha-Gal Conjugated Receptor-specific Glycopolymers. Bioorganic & Medicinal Chemistry 1999, vol. 7, pp. 1549-1558.*

Aigner et al. CD24, a Mucin-Type Glycoprotein, Is a Ligand for P-Selectin on Human Tumor Cells. Blood 1997, vol. 89, pp. 3385-3395.*

LaTemple et al. Synthesis of alpha-Galactosyl Epitopes by Recombinant alpha1,3Galactosyltransferase for Opsonization of Human Tumor Cell Vaccines by Anti-Galactose. Cancer Research 1996, vol. 56, pp. 3069-3074.*

Fong et al. Altered peptide ligand vaccination with Flt3 ligand expanded dendritic cells for tumor immunotherapy. Proceedings of the National Academy of Sciences of the United States of America 2001, vol. 98, No. 15, pp. 8809-8814.*

(Continued)

*Primary Examiner* — Louise Humphrey

(74) *Attorney, Agent, or Firm* — Knobbe Martens Olson & Bear, LLP

(57) ABSTRACT

The present invention is directed to ligand/receptor and antigen/antibody specificity exchangers comprising a saccharide or glycoconjugate. Methods of making these specificity exchangers and methods of using said specificity exchangers to treat or prevent human disease are described herein.

36 Claims, 4 Drawing Sheets

U.S. PATENT DOCUMENTS

| | | | |
|---|---|---|---|
| 6,090,388 | A | 7/2000 | Wang |
| 6,090,944 | A | 7/2000 | Hutchinson |
| 6,093,539 | A | 7/2000 | Maddon et al. |
| 6,245,895 | B1 | 6/2001 | Sällberg |
| 6,303,120 | B1 | 10/2001 | Danishefsky et al. |
| 6,417,324 | B1 | 7/2002 | Sällberg |
| 6,458,937 | B1 | 10/2002 | Bertozzi et al. |
| 6,469,143 | B2 | 10/2002 | Sällberg |
| 6,485,726 | B1 | 11/2002 | Blumberg et al. |
| 6,660,842 | B1 | 12/2003 | Sällberg |
| 7,033,594 | B2 | 4/2006 | Low et al. |
| 7,318,926 | B2 | 1/2008 | Sällberg et al. |
| 7,332,166 | B2 | 2/2008 | Sällberg et al. |
| 7,422,746 | B2 | 9/2008 | Mullis |
| 7,645,743 | B2 | 1/2010 | Mullis |
| 7,850,975 | B2 | 12/2010 | Mullis |
| 2002/0025513 | A1 | 2/2002 | Sällberg |
| 2002/0058247 | A1 | 5/2002 | Sällberg |
| 2003/0021789 | A1 | 1/2003 | Xu et al. |
| 2003/0044418 | A1 | 3/2003 | Davis et al. |
| 2004/0001853 | A1 | 1/2004 | George et al. |

FOREIGN PATENT DOCUMENTS

| | | |
|---|---|---|
| EP | 0 508 427 | 10/1992 |
| EP | 0510949 B2 | 4/2003 |
| JP | 04347162 | 12/1992 |
| WO | WO 93/15210 | 8/1993 |
| WO | WO 93/17044 | 9/1993 |
| WO | WO 94/13804 | 6/1994 |
| WO | WO 95/08577 | 3/1995 |
| WO | WO 95/22249 | 8/1995 |
| WO | WO 95/24924 A1 | 9/1995 |
| WO | WO 95/29938 | 11/1995 |
| WO | WO 98/03543 | 1/1998 |
| WO | WO 98/31389 | 7/1998 |
| WO | WO 98/34957 | 8/1998 |
| WO | WO 98/43677 | 10/1998 |
| WO | WO 99/27109 | 6/1999 |
| WO | WO 99/61041 | 12/1999 |
| WO | WO 99/66957 | 12/1999 |
| WO | WO 00/26385 | 5/2000 |
| WO | WO 00/66621 | 11/2000 |
| WO | WO 01/81421 | 11/2001 |
| WO | WO 01/82546 | 11/2001 |
| WO | WO 02/24887 | 3/2002 |
| WO | WO 03059251 A2 | 7/2003 |
| WO | WO 2005079423 A2 | 9/2005 |

OTHER PUBLICATIONS

LaTemple, et al., "Increased Immunogenicity of Tumor Vaccines Complexed with Anti-Gal: Studies in Knockout Mice for α1, 3Galactosyltransferase," *Cancer Research*, 59:3417-3423 (Jul. 15, 1999).

Urban, et al., "Tumor Antigens," *Annual Review of Immunology, Annual Reviews Inc.*, vol. 10, 1, pp. 617-644, Jan. 1992.

Yip, et al., "Identification of epitope regions recognized by tumor inhibitory and stimulatory anti-ErbB-2 monoclonal antibodies: implications for vaccine design," *Journal of Immunology*, vol. 166, No. 8, pp. 5271-5278, Apr. 15, 2001.

Lord, et al., "Binding of Fibrinogen Aα1-50-β-Galactosidase Fusion Protein to Thrombin Stabilizes the Slow Form," *J. of Biol. Chem.*, vol. 270, No. 42, pp. 24790-24793, 1995.

Barbas et al., "Assembly of combinatorial antibody libraries on phage surfaces: The gene III site," *Proc. Natl. Acad. Sci. USA*, 88:7978-7982 (1991).

Bianchi, et al., "Affinity Purification of a Difficult-Sequence Protein: Implications for the Inclusion of Capping in Synthetic-Protocols." *Int. J. Pept. Protein Res.*, 42(1):93-96, Jul. 1993.

Bianchi, et al., "Chemical Synthesis of a Designed Beta-Protein Through the Flow-Polyamide Method" *Int. J. Pept Protein Res.*, 41(4):385-393, Apr. 1993.

Bichko et al., "Epitopes recognized by antibodies to denatured core protein of hepatitis B virus," *Mol. Immunol.*, 30(3):221-231, (1993).

Bour et al., The Human Immunodeficiency Virus Type 1 CD4 Receptor and its Central Role in Promotion of HIV-1 Infection, Microbiological Reviews, Mr. 1995, vol. 59, No. 1, p. 63-93.

Brett et al., "The invasin protein of *Yersinia* spp. provides co-stimulatory activity to human T cells through interaction with beta 1 integrins," *Eur. J. Immunol.*, 23(7):1608-1614 (1993).

Cello J, et al., "Identification of group-common linear epitopes in structural and nonstructural proteins of enteroviruses by using synthetic peptides," *J. Clin. Microbiol.*, 31(4):911-916 (1993).

Chien et al., "The two-hybrid system: A method to identify and clone genes for proteins that interact with a protein of interest," *Proc. Natl. Acad. Sci. USA* (1991) 88:9578-9582.

Chui et al., "Genetic remodeling of protein glycosylation in vivo induces autoimmune disease," PNAS 98(3):1142-1147 (2001).

Cohen J, et al., "Ligand binding to the cell surface receptor for reovirus type 3 stimulates galactocerebroside expression by developing oligodendocytes," *Proc Natl Acad Sci USA*, 87(13):4922-4926 (1990).

Colberre-Garapin et al., "A new dominant hybrid selective marker for high eukaryotic cells," *J. Molecular Biology*, 150:1-14 (1991).

Communications Pursuant to Article 96(2) EPC dated Jul. 5, 2006, from European Patent Application No. 04 708 416.5.

Database Genseq 'Online Jul. 31, 2000, Yeda Res & Dev Co Ltd: "Murine anti-Pab-421 IDI-1 mAb heavy chain CDR based Peptide IDI-H1", XP002183676, Accession AAY70799 (published in WO0023082).

Database Genseq 'Online! Jan. 8, 1993, Clonatec SA: "Hepatitis B virus HBc antigen II", XP002183674 Accession AAR25272 (published in EP494825).

Database Genseq 'Online! Jul. 1, 1993, Cytel Corp: "Cytotoxic T-lymphocyte inducing peptide 802.02." XP002183675, Accession AAR33488.

Database Genseq 'Online! Oct. 21, 1991, Asahi Chemical Ind KK: "L-chain variable region of plasminogen activator antibody" XP002183673, Accession AAP61027 (published in JP11729000).

Database Patent_PRT 'Online! Mar. 21, 2001. Eurodiagnostica AB: "Sequence 9 from Patent WO0116163", XP002183677, Accession AX 090806.

Database WPI, Section Ch, Week 199713, Derwent Publications Ltd., London, GB: Class B04, AN 1997-140911, XP002183678 & JP 09 020798 A (Asahi Kasei Kogyo, KK), Jan. 21, 1997 abstract.

Doolittle R.F. et al., "The Amino Acid Sequence of the α-Chain of Human Fibrinogen," (1979) *Nature*, vol. 280, p. 464-468.

Ennas et al., "Human ALL-1/MII/HRX Antigen is Predominantly Localized in the Nucleus of Resting and Proliferating Peripheral Blood Mononuclear Cells" Cancer Research 57, 2035-2041, May 15, 1997.

Felding-Habermann et al., "Role of β3 Integrins in Melanoma Cell Adhesion to Activated Platelets under Flow," *J. Biol. Chem.*, 271(10):5892-5900 (1996).

Flock, "Extracellular-Matrix-Binding Proteins as Targets for the Prevention of *Staphylococcus aureus* Infections," (1999) *Molecular Medicine Today*, vol. 5 pp. 532-537.

Galili et al., "Enhancement of antigen presentation of influenza virus hemagglutinin by the natural human anti-Gal antibody," *Vaccine* (1996) 14(4):321-326.

Galili et al., "Evolutionary relationship between the natural anti-Galantibody and the Galα1→3Ga1 epitope in primates" Proc Natl. Acad. Sci. vol. 84, pp. 1369-1373, Mar. 1987 Immunology.

Galili et al., "One percent of human circulating B Lymphocytes are capable of producing the natural anti-gal antibody" Blood, vol. 82, No. 8, Oct. 15, 1993 pp. 2485-2493.

Galili et al., Human natural anti-α-galactosyl IgG: the specific recognition of α(1→3)-linked galactose residues, J. Exp. Med., vol. 162, Aug. 1985, pp. 573-582.

Ganem, "Hepadnaviridae and Their Replication," *Fields Virology*, Third Ed., Ch. 85, pp. 2703-2705, 1996.

GenCore sequence alignment of SEQ ID No. 16 with the L-chain variable region of plasminogen activator antibody of JP61172900-A, Ashi Chemical Ind. KK. Apr. 8, 1986, ID No. p. 61027.

Grabowska et al., "Identification of type-specific domains within glycoprotein G of herpes simplex virus 2 (HSV-2) recognized by the majority of patients infected with HSV-2, but not by those infected with HSV-1," *Journal of General Virology*, 80(7):1789-1798 (1999).

Greenspan et al., "Defining epitopes: It's not as easy as it seems," *Nature Biotechnology*, vol. 17, pp. 936-937, Oct. 1999.

Haseltine "Replication and Parthogenesis of the AIDS Virus," *Journal of Acquired Immune Deficiency Syndromes*, 1(3):217-240 and 231-236 (1988).

Henschen A. et al., "Preliminary Note on the Completion of the β-Chain Sequence", (1997) *Z. Physiol. Chem.*, 358:1643-1646.

Hollinger et al., "'Diabodies': Small Bivalent and Bispecific Antibody Fragments," *Proc. Natl. Acad. Sci. USA*, 90:6444-6448, Jul. 1993.

Huse et al., "Generation of a large combinatorial library of the immunologlobulin repertoire in Phage Lambda," iScience, 246:1275-1281 (1989).

Jin et al., "Expression, Isolation, and Characterization of the Hpatitis C Virus ATPase/RNA Helicase," *Archives of Biochemistry and Biophysics*, 323:47-53 (1995).

Katada et al., "A Novel Peptide Motif for Platelet Fibrinogen Receptor Recognition," *J. Biol. Chem.*, 272(12):7720-7226 (1997).

Korba and Gerin, "Use of a standardized cell culture assay to assess activities of nucleoside analogs against hepatitis B virus replication," *Antiviral Res.*, 19(1):55-70 (1992).

Korba and Milman, "A cell culture assay for compounds which inhibit hepatitis B virus replication," *Antiviral Res.*, 15(3):217-228 (1991).

Kreitman et al., "Immunotoxins for targeted cancer therapy," *Advanced Drug Delivery Reviews*, 31:53-88 (1998).

Lanza et al., Active immunity against the CD4 receptor by using an antibody antigenized with residues 41-55 of the first extracellular domain. Proceedings of the National Academy of Sciences of the United States of America (Washington, DC), Dec. 1993, vol. 90, pp. 11683-11687.0.

Lazdina et al., "Molecular basis for the interaction of the Hepatitis B virus core antigen with the surface immunoglobulin receptor on naïve B cells," *Journal of Virology* (2001) 75(14):6367-6374.

Leanna & Hannick, "The reverse two-hybrid system: a genetic scheme for selection against specific protein/protein interactions," *Nucl. Acid. Res.*, 24(17):3341-3347 (1996).

Lee et al., "Predominant Etiologic Association of Hepatitis C Virus with Hepatocellular Carcinoma Compared with Hepatitis B Virus in Elderly Patients in a Hepatitis B-Endemic Area," *Cancer*, 72:2564-2567 (1993).

Leibiger H. et al.; "Structural characterization of the oligosaccharides of a human monoclonal anti-lipopolysaccharide immunoglobulin M."; Glycobiology, May 1998, vol. 8, No. 5, May 1998, pp. 497-507, XP008033789; ISSN: 0959-6658; abstract; tables 2,3; p. 502, right-hand column, paragraph 3—p. 503, left-hand column, paragraph 1.

Levi et al., "A Complementarity-Determining Region Synthetic Peptide Acts as a Miniantibody and Neutralizes Human Immunodeficiency Virus Type 1 in vitro," *Proc. Natl. Acad. Sci. USA*, 90:4374-4378, May 1993.

Lew et al., "Site-directed immune responses in DNA vaccines encoding ligand-antigen fusions," *Vaccine*, England, vol. 18, No. 16, pp. 1681-1685 (2000).

Li et al., "Adenovirus-mediated expression of pig α(1,3) Gal epitope on the surface of human tumor cells," *Cell Research*, 11(2):116-124 (2001), http://www.cell-research.com/20012/01-2-x1.html.

Lin S. S. et al.; "Differential recognition by proteins of alpha-galactosyl residues on endothelial cell surfaces."; Clycobiology, May 1998, vol. 8, No. 5, May 1998, pp. 433-443, XP008033788; ISSN:0959-6658; abstract; table 1.

Lottspeich F. et al., "Preliminary Note on the Completion of the γ-Chain Sequence," (1977) *Z. Physiol. Chem.*, 358:935-938.

Lowman HB, "Bacteriophage display and discovery of peptide leads for drug development," *Annu. Rev. Biophys. Biomol. Struct.*, 26:401-424 (1997).

Luning et al., "Solid Phase Synthesis of the Fibronectin Glycopeptide V(Gal beta 3GalNAc alpha)THPGY, its Beta Analogue, and Corresponding Unglycosylated Peptide," Glycoconjugate Journal, Dec. 1991, vol. 8(6), pp. 450-455.

Machida A, et al., "Antigenic sites on the arginine-rich carboxyl-terminated domain of the capsid protein of hepatitis B virus distinct from hepatitis B core or e antigen," *Mol. Immunol.*, 26(4):431-421 (1989).

McDevitt et al., "Identification of the ligand-binding domains of the surface-located fibrinogen receptor (clumping factor) of *Staphylococcus aureaus*,"Molecular Microbiology, 165(5):895-907 (1995).

McDevvit et al., "Characterization of the interaction between the *Staphylococcus aureus* clumping factor (ClfA) and fibrinogen," *Eur. J. Biochem.* 247(1):416-424 (1997).

Milich et al., "Role of B cells in antigen presentation of the hepatitis B core," *Proc. Natl. Acad. Sci. USA*, 94:14648-14653. 1997.

Milich et al., "The humoral immune response in acute and chronic hepatitis B virus infection," *Springer Semin. Immunopathol.*, 17:149-166 (1995).

Milich et al., "The Nucleocapsid of Hepatitis B Virus is Both a T-Cell-Independent and a T-Cell-Dependent Antigen," *Science*, 234:1398-1401 (1986).

Mizukami T. et al.; "Binding region for human immunodeficiency virus (HIV) and epitopes for HIV-blocking monoclonal antibodies of the CD4 molecule defined by site-directed mutagenesis." Proceedings of the National Academy of Sciences of the United States of America, Dec. 1998, vol. 85, No. 23, Dec. 1988, pp. 9273-9277, XP001194700; ISSN:0027-8424; cited in the application; abstract; figure 1.

Mollick et al., "Localization of a Site on Bacterial Superantigens That Determines T Cell Receptor 3 Chain Specificity," *J. Exp. Med.*, 177:283-293 (1993).

Morrison et al., "Chimeric human antibody molcules: mouse antigen-binding domains which human constant region domains," *Proc. Natl. Acad. Sci. USA*, 81(21):6851-6855 (1984).

Neuberger et al., "Recombinant antibodies possessing novel effector functions," *Nature*, 312:604-608 (1984).

Ogg et al., "Sensitization of tumour cells to lysis by virus-specific CTL using antibody-targeted MHC class I/peptide complexes," *British Journal of Cancer*, 82(5):1058-1062 (2002).

Owens et al., "Mapping the Collagen-Binding Site of Human Fibronectin by Expression in *Escherichia coli*," *Embo Journal*, IRL Press, Eynsham, GB, vol. 5, No. 11, pp. 2825-2830 (1986).

P.R. Wood, H.-F. Seow, "T cell cytokines and disease prevention," *Veterinary Immunology and Immunopathology*, 54(1996) pp. 33-44.

Pei et al., "Functional Studies of a Fibrinogen Binding Protein from *Staphylococcus epidermidis*," (1999) *Infection and Immunity*, p. 4525-4530.

Prange et al., "Chaperones Involved in hepatitis B virus morphogenesis," *Biol. Chem.*, Mar 1999, 380(3):305-314.

Ramberg, "The Nutrition Science Site: Glyconutritionals," http://glycoscience.com/glycoscience/document_viewer.wm?&ID-719 (2000).

Roivanen et al., "Antigenic regions of poliovirus type 3/Sabin capsid proteins recognized by human sera in the peptide scanning technique," *Virology*, 180:99-107 (1991).

Rudd et al., "Glycosylation and the Immune System," *Science*, 291:2370-2376 (2001) http://sciencemag.org.

Rüther and Müller-Hill, "East identification of cDNA clones," *EMBO Journal*, 2(10):1791-1794 (1983).

Salfeld J, et al., "Antigenic determinants and functional domains in core antigen and e antigen from hepatitis B virus," *Journal of Virology*, 63(2):798-808 (1989).

Sällberg et al., "Characterization of linear binding site for a monoclonal antibody to hepatitis B core antigen," *J. Med. Virol.* 33(4):248-252 (1991).

Sällberg et al., "Human and murine B-cells recognize the HBeAg/beta (or HBe2) epitope as a linear determinant," *Mol. Immunol.* 28(7):719-726 (1991).

Sällberg et al., "Rapid 'tea-bag' peptide synthesis using 9-fluorenlymethoxycarbonyl (Fmoc) protected amino acids applied for antigenic mapping of viral proteins," *Immunology Letters*, 30:59-68, 1991.

Sällberg et al., "Synthetic peptides as mini antibodies," Peptides: Chemistry and Biology, eds/ Hodges, R. and J. Rivier, ESCOM, Leiden, pp. 715-718 (1993).

Sällberg et al., "The Antigen/Antibody Specificity Exchanger: A New Peptide Based Tool for Re-directing Antibodies of Other Specificities to Recognize the V3 Domain of HIV-1 GP120," *Biochemical and Biophysical Research Communications*, 205:1386-1390 (1994).

Sällberg et la., "Immunochemical structure of the carboxy-terminal part of hepatitis B e antigen: identification of internal and surface-exposed sequences," *Journal of General Virology*, 74: 1335-134, 1993.

Sällberg M. "Ligand/Receptor Specificity Exchangers that redirect Antibodies to Receptors on a Pathogen," U.S. Appl. No. 09/664,945, filed Sep. 19, 2000.

Sällberg M. "Ligand/Receptor Specificity Exchangers that redirect Antibodies to Receptors on a Pathogen," U.S. Appl. No. 09/664,025, filed Sep. 19, 2000.

Sällberg M. "Synthetic Peptides That Bind to the Hepatitis B Virus Core and E Antigens," U.S. Appl. No. 10/153,271, filed May 21, 2002.

Saragovi, et al., "Design and Synthesis of a Mimetic from an Antibody Complementarity-Determining Region" *Science*, 253:792-795, Aug. 16, 1991.

Schödel, et al., "Structure of Hepatitis B Virus Core and e-Antigen," *The Journal of Biological Chemistry*, 268:1332-1337, 1993.

Sears et al., "Toward Automated Synthesis of Oligosaccharides and Glycoproteins," Science, vol. 291, pp. 2344-2350, Mar. 23, 2001, http://www.sciencemag.org.

Seitz et al., Glycopeptide synthesis and the effects of glycosylation on protein structure and activity, Chembiochem 2000, vol. 1, pp. 214-246.

Sequence alignment of Genseq sequence alignment of instant SEQ ID No. 28 with the antihuman parathyroid hormone-related protein of JP04228089-A, Kaneka Corp., Aug. 18, 1992, ID No. AR27008.

Sequence alignment of Genseq sequence alignment of instant SEQ ID No. 29 with anti-DNA antibody 7b3 heavy chain variable region of WO 96/36361-A1, University of Michigan, Aug. 12, 1997, ID No. AAW04593.

Sequence alignment of Genseq sequence alignment of instant SEQ ID No. 33 with anti-proenkephalin antibody PE-19 of WO 9606863-A1, University of Dundee, Oct. 9, 1996, ID No. AAR91370.

Signals Magazine: Buzz-Glycosylation Matters Jun. 6, 2002, http://www.signalsmag.com/signalsmag.nsf/0/A08BFCD7912B34F88256BCE0011B41A.

Skrivelis et al., "The structure of the variable regions of mouse monoclonal antibodies to hepatitis B virus core antigens," *Scand. J. Immunol.* (1993) 37:637-643.

Steinbergs et al., "Structure of the variable regions of the monoclonal antibody 13D3 that recognizes a linear epitope spanning the C-terminus of hepatitis B e antigen," *Proceedings of the Latvian Academy of Sciences* (1996) 50(2):74-77.

Takahashi et al., "Acute hepatitis in rates expressing human hepatitis B virus transgenes," *Proc. Natl. Acad. Sci. USA*, 92:1470-1474 (1995).

Takeda et al., "Construction of chimaeric processed immunoglobulin genes containing mouse variable and human constant region sequences," Nature, 314:452-454 (1985).

Taub R. et al, "A monoclonal antibody against the platelet fibrinogen receptor contains a sequence that mimics a receptors recognition domain in fibrinogen," J. Biol. Chem., 264(1):259-265(1989).

The Columbia Encyclopedia, Sixth Edition, Copyright 2002, Columbia University Press, http://www.bartleby.com/gl/glycopro.html.

Tramontano et al., "The Making of the Minibody: An Engineered Beta-Protein for the Display of Conformationally Constrained Peptides," J. of Molecular Recognition, 7(1):9-24 (1994).

Watt K.W.K. et al., "Amino Acid Sequences Studies on the αChain of Human Fibrinogen Overlapping Sequences Providing the Complete Sequence," (1979) Biochemistry, vol. 18, pp. 5410-5416.

Williams et al., "Design of bioactive peptides based on antibody hypervariable region structures. Development of conformationally constrained and dimeric peptides with enhanced affinity," *Biol. Chem*., 266(8):5182-5190 (1991).

Williams et al., "Development of biologically active peptides based on antibody structure," *Proc. Natl. Acad. Sci. USA*, 86(14):5537-5541 (1989).

Winter and Milstein, "Man-made antibodies," Nature, 349(6307):293-299 (1991).

Zanetti M., "Antigenized Antibodies" *Nature*, 355: 476-477, Jan. 30, 1992.

Zhang et al., "Characterization of a monoclonal antibody and its single-chain antibody fragment recognizing the nucleoside triphosphate/helicase domain of the hepatitis C virus nonstructural 3 protein," *Clin. Diagn. Lab. Immunol.*,7(1):58-63 (2000).

Zhang et al., "Molecular basis for antibody cross-reactivity between the hepatitis C virus core protein and the hos-derived GOR protein," *Clin. Exp. Immunol*, 96(3):403-409 (1994).

Office Action in U.S. Appl. No. 10/773,628, filed Feb. 5, 2004.

Office Action in U.S. Appl. No. 10/913,754, filed Aug. 6, 2004.

Office Action in U.S. Appl. No. 11/411,294, filed Apr. 26, 2006.

Ashford et al. Site-specific glycosylation of recombinant rat and human soluble CD4 variants expressed in Chinese Hamster Ovary cells. The Journal of Biological Chemistry Feb. 15, 1993, vol. 268, No. 5, p. 3260-3267.

Watt K.W.K. et al., "Amino acid sequence of the β chain of human fibrinogen," *Biochemistry* (1979) 18(1):68-76.

Wong et al. Synthetic glycosylation of proteins using N-(B-saccharide) iodacetamides: applications in site-specific glycosylation and solid-phase enzymic oligosaccharide synthesis. Biochemistry Journal 1994, vol. 300, p. 843-850.

Perdomo, et al., "Neutralization of HIV-1 b redirection of natural antibodies," *Proc. Natl. Academy of Sciences*, 105(34):12515-12520 (2008).

* cited by examiner

GLYCOSYLATED SPECIFICITY EXCHANGERS

CROSS-REFERENCE TO RELATED APPLICATIONS

This application is a continuation of U.S. application Ser. No. 11/930,860, filed on Oct. 31, 2007, now abandoned, which is a continuation of U.S. application Ser. No. 10/773,628, filed on Feb. 5, 2004, now U.S. Pat. No. 7,318,926, which claims the benefit of priority of U.S. provisional patent application No. 60/446,172, filed Feb. 6, 2003, which is hereby expressly incorporated by reference in its entirety.

FIELD OF THE INVENTION

The present invention generally relates to compositions and methods for preventing and treating human diseases, including cancer, and those resulting from pathogens such as bacteria, yeast, parasites, fungus, viruses, and the like. More specifically, embodiments described herein concern the manufacture and use of specificity exchangers comprising glycosylated antigenic domains, which redirect natural antibodies that are present in a subject to a pathogen.

BACKGROUND OF THE INVENTION

Specificity exchangers are generally composed of two domains, a specificity domain and an antigenic domain. There are two general types of specificity exchangers differentiated by the nature of their specificity domains. (See e.g., U.S. Pat. No. 6,933,366, hereby expressly incorporated by reference in its entirety). The first type of specificity exchanger is an antigen/antibody specificity exchanger. Several different types of antigen/antibody specificity exchangers can be made. (See e.g., U.S. Pat. Nos. 5,869,232; 6,040,137; 6,245,895; 6,417,324; 6,469,143; and U.S. Patent Publication No. 20020058247; and International App. Nos. PCT/SE95/00468 and PCT/IB01/00844, all of which are hereby expressly incorporated by reference in their entireties).

Antigen/antibody specificity exchangers comprise an amino acid sequence of an antibody that specifically binds to an antigen (i.e., the specificity domain) joined to an amino acid sequence to which an antibody binds (i.e., the antigenic domain). Some specificity domains of antigen/antibody specificity exchangers comprise an amino acid sequence of a complementarity determining region (CDR), are at least 5 and less than 35 amino acids in length, are specific for HIV-1 antigens, or are specific for hepatitis viral antigens. Some antigenic domains of antigen/antibody specificity exchangers comprise a peptide having an antibody-binding region of viral, bacterial, or fungal origin, are at least 5 and less than 35 amino acids in length, or contain peptides (e.g., peptides comprising epitopes) that are obtained from polio virus, measles virus, hepatitis B virus, hepatitis C virus, or HIV-1.

A second type of specificity exchanger, the ligand/receptor specificity exchanger, is also composed of a specificity domain and an antigenic domain, however, the specificity domain of the ligand/receptor specificity exchanger comprises a ligand for a receptor that is present on a pathogen, as opposed to a sequence of an antibody that binds to an antigen. That is, a ligand/receptor specificity exchanger differs from an antibody/antigen specificity exchanger in that the ligand/receptor specificity exchanger does not contain a sequence of an antibody that binds an antigen but, instead, adheres to the pathogen vis a vis ligand interaction with a receptor that is present on the pathogen. Several different types of ligand/receptor specificity exchangers can be made. (See e.g., U.S. Pat. Nos. 6,660,842 and 6,933,366; and International App. No. PCT/IB01/02327, all of which are hereby expressly incorporated by reference in their entireties).

Some specificity domains of ligand/receptor specificity exchangers comprise an amino acid sequence that is a ligand for a bacterial adhesion receptor (e.g., extracellular fibrinogen binding protein or clumping factor A or B), are at least 3 and less than 27 amino acids in length, or are specific for bacteria, viruses, or cancer cells. Some antigenic domains of ligand/receptor specificity exchangers comprise a peptide having an antibody-binding region of a pathogen or toxin, are at least 5 and less than 35 amino acids in length, or contain peptides that are obtained from polio virus, TT virus, hepatitis B virus, and herpes simplex virus. Despite these advances in medicine, there remains a need for more specificity exchangers that redirect antibodies present in an individual to a target molecule.

BRIEF SUMMARY OF THE INVENTION

Aspects of the invention concern a specificity exchanger comprising a specificity domain that is less than 200 amino acids in length joined to at least one saccharide. In some embodiments the saccharide is a Gal antigen, preferably, Gal α (1,3) Gal β. These specificity exchangers can be ligand/receptor specificity exchangers or antigen/antibody specificity exchangers. Although the saccharide can be directly joined to the specificity domain such that there is no antigenic domain or linker, some embodiments include an antigenic domain and/or linker in addition to the saccharide.

Some embodiments of the specificity exchangers described herein bind to a bacteria (e.g., Staphylococcus), a virus (e.g., hepatitis A virus (HAV), hepatitis B virus (HBV), hepatitis C virus (HCV), influenza virus, and human immunodeficiency virus (HIV)) or a cancer cell. Preferred specificity exchangers are directed to HIV and the specificity domains of these embodiments can comprise a CD4 or CDR peptide (e.g., a sequence selected from the group consisting of SEQ. ID. No. 1, SEQ. ID. No. 2, SEQ. ID. No. 3, SEQ. ID. No. 4, SEQ. ID. No. 5, SEQ. ID. No. 6, SEQ. ID. No. 7, SEQ. ID. No. 8, and SEQ. ID. No. 9) and said at least one saccharide is Gal α (1,3) Gal β. The specificity exchangers described above can have a specificity domain that is less than 150, 100, 50, or 25 amino acids in length. The specificity exchangers described herein can be used to reduce the proliferation of bacteria, virus or cancer cells in a subject in need thereof and to prepare medicaments and pharmaceuticals for this purpose.

DETAILED DESCRIPTION OF THE INVENTION

Figure 1:
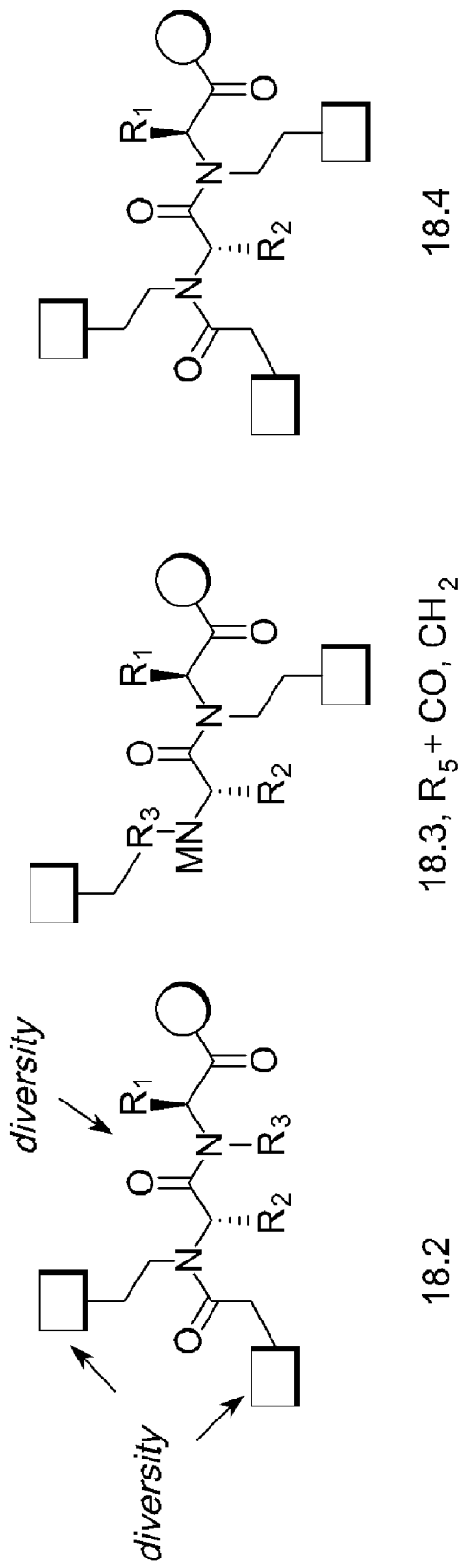
FIG. 1 illustrates a method that can be employed to artificially synthesize glycopeptide libraries.
Figure 1:
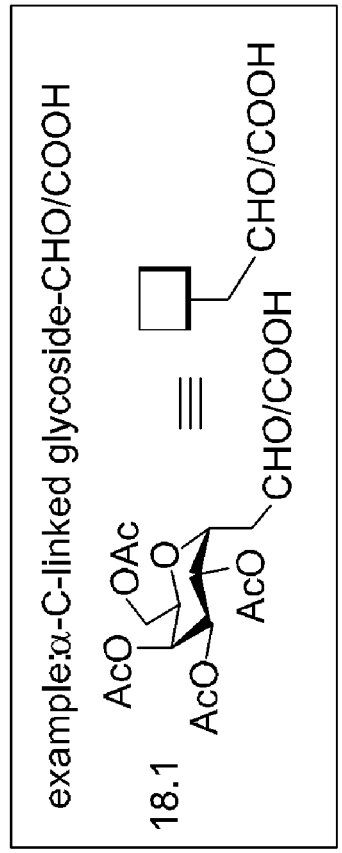

It has been discovered that antibody/antigen specificity exchangers and ligand/receptor specificity exchangers (collectively referred to as "specificity exchangers") that comprise saccharides or glycoconjugates (e.g., blood group sugars) react strongly to antibodies that are naturally present in a subject and thereby promote the redirection of said antibodies to a pathogen. Aspects of the invention concern specificity exchangers (e.g., antibody/antigen specificity exchangers and ligand/receptor specificity exchangers) that comprise a saccharide, preferably a blood group sugar and more preferably a gal-α-1-3 gal β sugar. Embodiments also include pharmaceuticals comprising said specificity exchangers, which can be used to treat human disease, such as infection by a pathogen or cancer. Accordingly, methods of making said glycosylated specificity exchangers and using said specificity exchangers to redirect antibodies to a molecule present on a pathogen, for example, are embodiments.

Specificity exchangers comprise a specificity domain and an antigenic domain. The length of the specificity domain of the specificity exchangers is desirably between at least 3-200 amino acids, preferably between at least 5-100 amino acids, more preferably between 8-50 amino acids, and still more preferably between 10-25 amino acids. The length of the antigenic domain of the specificity exchangers is desirably between at least 3-200 amino acids, preferably between at least 5-100 amino acids, more preferably between 8-50 amino acids, and still more preferably between 10-25 amino acids. In some embodiments, however, the specificity exchanger comprises only a glycosylated specificity domain (e.g., a portion of an antibody directed to a pathogen or a ligand for a receptor on a pathogen) such that the glycosylation region itself serves as the antigenic domain. That is, some aspects of the invention described herein concern specificity exchangers (i.e., antigen/antibody and ligand/receptor specificity exchangers) that comprise specificty domains directed to epitopes or receptors present on a pathogen or cancer cell, wherein said specificity domains are joined to one or more sugars (e.g., a glycosylation domain having one or more gal-α-1-3 gal β sugars) that is itself an antigenic domain that interacts with antibodies that are naturally present in a subject.

The specificity exchangers described herein comprise specificity domains that interact with antigens or receptors on pathogens, including, but not limited to, bacteria, yeast, parasites, fungus, cancer cells, and pathogenic peptides. Some embodiments, for example, comprise a sequence obtained from an antibody that binds to a bacteria, hepatitis virus (e.g., HAV, HBV, or HCV), HIV, flu viruses such as influenza virus, cancer cell epitopes, and peptides associated with human disease (e.g., prion peptides, Alzheimer's peptides (Aβ), and neuropeptides). Other embodiments have a specificity domain that comprises a fragment of an extracellular matrix protein (e.g., between 3 and 14 amino acids, such as 3 to 5, 8, 9, 10, 12, or 14 consecutive amino acids of fibrinogen), a ligand for a receptor on a virus (e.g., HAV, HBV, HCV, HIV, influenza virus), or a ligand for a receptor on a cancer cell or pathogenic peptide. In preferred embodiments, for example, the specificity domain comprises a ligand that is a fragment (e.g., between 3 and 20 amino acids, such as 3 to 5, 8, 9, 10, 12, 14, 17, and 20 consecutive amino acids) of an extracellular matrix protein selected from the group consisting of fibrinogen, collagen, vitronectin, laminin, plasminogen, thrombospondin, and fibronectin. Several of the specificity exchangers described herein bind to a receptor found on a pathogen (vis a vis antigen/antibody interaction or ligand/receptor interaction). In some embodiments, the receptor is a bacterial adhesion receptor, for example, a bacterial adhesion receptor selected from the group consisting of extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein. The next section describes specificity domains of Antigen/Antibody specificity exchangers in greater detail.

Specificity Domains of Antigen/Antibody Specificity Exchangers

The specificity domain of antigen/antibody specificity exchangers can include the amino-acid sequence of any antibody that specifically binds to a certain antigen, such as a hapten, for example. Preferred specificity domains of antigen/antibody specificity exchangers comprise an amino acid sequence of a complementarity determining region (CDR) or a framework region of a certain antibody. The CDRs of antibodies are responsible for the specificity of the antibody. X-ray crystallography has shown that the three CDRs of the variable (V) region of the heavy chain and the three CDRs of the V region of the light chain may all have contact with the epitope in an antigen-antibody complex.

In certain embodiments, single peptides corresponding to the CDRs of mAbs to various antigens and that are capable of mimicking the recognition capabilities of the respective mAb can be included in the specificity domain of the antigen/antibody specificity exchangers. Specifically, a peptide corresponding to CDRH3 of a mAb specific for the V3 region of HIV-1 gp160 or a portion of an antibody specific for a region of gp120 that interacts with CD4 can be included in the specificity domain. The peptide directed to the V3 region of HIV-1 was shown to have neutralizing capacity when assayed in vitro. The CDRH3 can be derived from mAb F58, and Ab C1-5, and the like. Like CDRH3, the CDRH1 and/or CDRH2 domain of Ab C1-5 can also be used in the specificity domains described herein. In other embodiments the specificity domain can include a peptide corresponding to CDRH2 of a mAb to hepatitis B virus core antigen (HBcAg). CDRH2 has demonstrated an ability to capture HBcAg. Several other peptides, derived from antibodies that bind HBcAg or hepatitis B virus e antigen (HBeAg) have been identified. (See U.S. Pat. No. 6,417,324, issued Jul. 9, 2002; and U.S. Patent Publication No. 20020058247 and U.S. Patent Publication No. 20030082186, all of which are hereby incorporated by reference in their entireties). These peptides (specificity domains) can be incorporated into antigen/antibody specificity exchangers so as to redirect antibodies present in a subject to hepatitis B virus. The next section describes specificity domains for ligand/receptor specificity exchangers in greater detail.

Specificity Domains for Ligand/Receptor Specificity Exchangers

The diversity of ligand/receptor specificity exchangers is also equally vast because many different ligands that bind many different receptors on many different pathogens can be incorporated into a ligand/receptor specificity exchanger. The term "pathogen" generally refers to any etiological agent of disease in an animal including, but not limited to, bacteria, parasites, fungus, mold, viruses, and cancer cells. Similarly, the term "receptor" is used in a general sense to refer to a molecule (usually a peptide other than a sequence found in an antibody, but can be a carbohydrate, lipid, or nucleic acid) that interacts with a "ligand" (usually a peptide other than a sequence found in an antibody, or a carbohydrate, lipid, nucleic acid or combination thereof). The receptors contemplated do not have to undergo signal transduction and can be involved in a number of molecular interactions including, but not limited to, adhesion (e.g., integrins) and molecular signaling (e.g., growth factor receptors).

In certain embodiments, desired specificity domains include a ligand that has a peptide sequence that is present in an extracellular matrix protein (e.g., fibrinogen, collagen, vitronectin, laminin, plasminogen, thrombospondin, and fibronectin) and some specificity domains comprise a ligand that interacts with a bacterial adhesion receptor (e.g., extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein).

Investigators have mapped the regions of extracellular matrix proteins that interact with several receptors. (See e.g., McDevvit et al., *Eur. J. Biochem.*, 247:416-424 (1997); Flock, *Molecular Med. Today*, 5:532 (1999); and Pei et al., *Infect. and Immun.* 67:4525 (1999), all of which are herein expressly incorporated by reference in their entirety). Some receptors bind to the same region of the extracellular matrix protein, some have overlapping binding domains, and some bind to different regions altogether. Preferably, the ligands that make up the specificity domain have an amino acid sequence that has been identified as being involved in adhesion to an extracellular matrix protein. It should be understood, however, that random fragments of known ligands for any receptor on a pathogen can be used to generate ligand/receptor specificity exchangers and these candidate ligand/receptor specificity exchangers can be screened in the characterization assays described infra to identify the molecules that interact with the receptors on the pathogen.

Some specificity domains have a ligand that interacts with a bacterial adhesion receptor including, but not limited to, extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein. Ligands that have an amino acid sequence corresponding to the C-terminal portion of the gamma-chain of fibrinogen have been shown to competitively inhibit binding of fibrinogen to ClfA, a *Staphylococcus aureus* adhesion receptor. (McDevvit et al., *Eur. J. Biochem.*, 247:416-424 (1997)). Further, *Staphylococcus* organisms produce many more adhesion receptors such as Efb, which binds to the alpha chain fibrinogen, ClfB, which interacts with both the α and β chains of fibrinogen, and Fbe, which binds to the γ chain of fibrinogen. (Pei et al., *Infect. and Immun.* 67:4525 (1999)). Accordingly, preferred specificity domains comprise between 3 and 30 amino acids, that is, at least 3, 4, 5, 6, 7, 8, 9, 10, 11, 12, 13, 14, 15, 16, 17, 18, 19, 20, 21, 22, 23, 24, 25, 26, 27, 28, 29, or 30 consecutive amino acids of a sequence present in a molecule (e.g., fibrinogen) that can bind to a bacterial adhesion receptor.

Specificity domains can also comprise a ligand that interacts with a viral receptor. Several viral receptors and corresponding ligands are known and these ligands or fragments thereof can be incorporated into a ligand/receptor specificity exchanger. For example, Tong et al., has identified an Hepadnavirus receptor, a 170 kd cell surface glycoprotein that interacts with the pre-S domain of the duck hepatitis B virus envelope protein (U.S. Pat. No. 5,929,220) and Maddon et al., has determined that the T cell surface protein CD4 (or the soluble form termed T4) interacts with gp120 of HIV (U.S. Pat. No. 6,093,539); both references are herein expressly incorporated by reference in their entireties. Thus, specificity domains that interact with a viral receptor can comprise regions of the pre-S domain of the duck hepatitis B virus envelope protein (e.g., amino acid residues 80-102 or 80-104) or regions of the T cell surface protein CD4 (or the soluble form termed T4) that interacts with gp120 of HIV (e.g., the extracellular domain of CD4/T4 or fragments thereof). For example, ligand/receptor specificity domains directed to the CDR (V3 binding complement) or CD4 (gp120 binding complement) binding domains of HIV have been prepared. (See TABLE 1). Many more ligands for viral receptors exist and these molecules or fragments thereof can be used as a specificity domain.

TABLE 1

HIV specific ligand/receptor specificity domains

| Glycosylated Sp. exchanger Name | Sequence | Identifier |
|---|---|---|
| Gal-CDR | DCDLIYYDYEEDYYFDY | (Seq. Id. No. 1) |
| Gal-CD4-1 | DQFHWKNSNQIKILGN | (Seq. Id. No. 2) |
| Gal-CD4-4 | DQGSFLTKGPSKLNDR | (Seq. Id. No. 3) |
| Gal-CD4-100 | QFHWKNSNQIKILGN | (Seq. Id. No. 4) |
| Gal-CD4-101 | NSNQIKILGNQGSFL | (Seq. Id. No. 5) |
| Gal-CD4-102 | KILGNQGSFLTKGPS | (Seq. Id. No. 6) |
| Gal-CD4-103 | QGSFLTKGPSKLNDR | (Seq. Id. No. 7) |
| Gal-CD4-104 | TKGPSKLNDRADSRR | (Seq. Id. No. 8) |
| Gal-CD4-105 | KLNDRADSRRSLWDQ | (Seq. Id. No. 9) |

Specificity domains can also comprise a ligand that interacts with a receptor present on a cancer cell. The proto-oncogene HER-2/neu (C-erbB2) encodes a surface growth factor receptor of the tyrosine kinase family, p185HER2. Twenty to thirty percent of breast cancer patients over express the gene encoding HER-2/neu (C-erbB2), via gene amplification. Thus, ligand/receptor specificity exchangers comprising a specificity domain that encodes a ligand for HER-2/neu (C-erbB2) are desirable embodiments. Many types of cancer cells also over express or differentially express integrin receptors. Many preferred embodiments comprise a specificity domain that interacts with an integrin receptor. Although integrins predominantly interact with extracellular matrix proteins, it is known that these receptors interact with other ligands such as invasins, RGD-containing peptides (i.e., Arginine-Glycine-Aspartate), and chemicals. (See e.g., U.S. Pat. Nos. 6,090,944 and 6,090,388; and Brett et al., *Eur J Immunol,* 23:1608 (1993), all of which are hereby expressly incorporated by reference in their entireties). Ligands for integrin receptors include, but are not limited to, molecules that interact with a vitronectin receptor, a laminin receptor, a fibronectin receptor, a collagen receptor, a fibrinogen receptor, an integrin receptor. The next section describes some of the antigenic domains that can be used with the specificity exchangers described herein.

Antigenic Domains The diversity of antigenic domains that can be used in the ligand/receptor specificity exchangers and antibody/antigen specificity exchangers is quite large because a pathogen or toxin can present many different epitopes. Desirably, the antigenic domains used with the specificity exchangers are peptides obtained from surface proteins or exposed proteins from bacteria, fungi, plants, molds, viruses, cancer cells, and toxins. It is also desired that the antigenic domains comprise a peptide sequence that is rapidly recognized as non-self by existing antibodies in a subject, preferably by virtue of naturally acquired immunity or vaccination. For example, many people are immunized against childhood diseases including, but not limited to, small pox, measles, mumps, rubella, and polio. Thus, antibodies to epitopes on these pathogens can be produced by an immunized person. Desirable antigenic domains have a peptide that contains one or more epitopes that is recognized by antibodies in the subject that are present in the subject to respond to pathogens such as small pox, measles, mumps, rubella, herpes, hepatitis, and polio.

Some embodiments, however, have antigenic domains that interact with an antibody that has been administered to the subject. For example, an antibody that interacts with an antigenic domain on a specificity exchanger can be co-administered with the specificity exchanger. Further, an antibody that interacts with a specificity exchanger may not normally exist in a subject but the subject has acquired the antibody by introduction of a biologic material or antigen (e.g., serum, blood, or tissue) so as to generate a high titer of antibodies in the subject. For example, subjects that undergo blood transfusion acquire numerous antibodies, some of which can interact with an antigenic domain of a specificity exchanger. Some preferred antigenic domains for use in a specificity exchanger also comprise viral epitopes or peptides obtained from pathogens such as the herpes simplex virus, hepatitis B virus, TT virus, and the poliovirus.

Preferably, the antigenic domains comprise an epitope or peptide obtained from a pathogen or toxin that is recognized by a "high-titer antibody." The term "high-titer antibody" as used herein, refers to an antibody that has high affinity for an antigen (e.g., an epitope on an antigenic domain). For example, in a solid-phase enzyme linked immunosorbent assay (ELISA), a high titer antibody corresponds to an antibody present in a serum sample that remains positive in the assay after a dilution of the serum to approximately the range of 1:100-1:1000 in an appropriate dilution buffer. Other dilution ranges include 1:200-1:1000, 1:200-1:900, 1:300-1:900, 1:300-1:800, 1:400-1:800, 1:400-1:700, 1:400-1:600, and the like. In certain embodiments, the ratio between the serum and dilution buffer is approximately: 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, 1:1000. Epitopes or peptides of a pathogen that can be included in an antigenic domain of a specificity exchanger include the epitopes or peptide sequences disclosed in Swedish Pat No. 9901601-6; U.S. Pat. No. 5,869,232; *Mol. Immunol.* 28: 719-726 (1991); and *J. Med. Virol.* 33:248-252 (1991); all which are herein expressly incorporated by reference in their entireties.

The antigenic domains of the specificity exchangers described herein do not have to be peptides, however. In some embodiments, the sugar, plurality of sugars, glycosylation region or glycosylation domain is itself the antigenic domain. That is, some embodiments are specificity exchangers (i.e., antigen/antibody and ligand/receptor specificity exchangers) that comprise a specificity domain that is joined to a sugar, a plurality of sugars, a glycosylation region, or a glycosylation domain with or without a peptide linker but lacking an antigenic peptide or epitope obtained from a pathogen or toxin. In this manner, glycosylated specificity domains (e.g., antigen/antibody and ligand/receptor specificity domains) are also referred to as glycosylated specificity exchangers, wherein the sugar, plurality of sugars, glycosylation region or glycosylation domain is itself the antigenic domain. The next section describes glycosylated specificity exchangers in greater detail.

Specificity Exchangers Comprising Saccharides and Glycoconjugates

Generally, the glycosylated specificity exchangers (i.e., antibody/antigen specificity exchangers and ligand/receptor specificity exchangers) comprise a specificity domain that is at least 3 and less than or equal to 200 amino acids in length joined to an antigenic domain (e.g., a peptide backbone) that is at least 3 and less than or equal to 200 amino acids in length or no peptide-based antigenic domain at all (i.e., the specificity domain is glycosylated itself with or without a linker but lacking an antigenic peptide obtained from a pathogen or containing an epitope of a pathogen). The antigenic domain and/or specificity domain can comprise a plurality of saccharides that, together with the peptide backbone or by itself, react with high titer antibodies that are naturally present in a human. Preferably, the glycosylation domain or region contains blood group sugars that are xenoactive antigens (e.g., blood group sugars that are the basis for hyperactute rejection of xenografts or transplantations).

In some embodiments, for example, the specificity exchangers comprise a specificity domain that is between or at least and/or less than or equal to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 amino acids in length, and said specificity domain is joined to an antigenic domain (e.g., a peptide backbone) that is between or at least and/or less than or equal to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 amino acids in length, wherein said antigenic domain or specificity domain or both comprise a plurality of saccharides. Other embodiments comprise a specificity domain that is between or at least and/or less than or equal to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 amino acids in length, and said specificity domain is joined to a plurality of saccharides (with or without a peptide linker and with or without a peptide or epitope of a pathogen or with or without an antigenic domain). Depending on the embodiment, the "plurality of saccharides" can include at least 2 and 10,000 or more sugar units. In some embodiments, for example, between or at least and/or less than or equal to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2250, 2500, 2750, 3000, 3250, 3500, 3750, 4000, 4250, 4500, 4750, 5000, 5250, 5500, 5750, 6000, 7000, 8000, 9000, 10,000 or more sugar units are joined to the specificity domain either directly or indirectly (e.g., through a support such as the peptide backbone of a linker an antigenic domain comprising a peptide or epitope of a pathogen).

The diversity of specificity domains that can be used in the specificity exchangers described herein is quite large because many different antibody/antigen and ligand/receptor interactions exist on a pathogen (e.g., a bacteria such as *Staphylococcus*). Preferred specificity domains are directed to bacterial adhesion proteins such as ClfA and ClfB or other bacterial receptors that interact with fragments of fibrinogen and specificity domains directed to viruses such as hepatitis, flu, and HIV. The diversity of antigenic domains that can be used in the specificity exchangers described herein is also quite large because many different supports and many different saccharides or groups of saccharides can be used. The term "saccharide" is intended to be construed broadly so as to non-exclusively encompass monosaccharides, disaccharides, polysaccharides (glycans), oligosaccharides, and other similar compounds. The term "glycoconjugate" is also to be construed broadly, and generally refers to an organic compound consisting of one or more carbohydrate units (e.g., a saccharide) joined to a support.

In several embodiments, the specificity domain is joined to a support to which a plurality of saccharides and/or a glycoconjugate is also joined. A "support" can be a peptide backbone, (e.g., an antigenic domain, as described above), a protein, a resin, or any macromolecular structure that can be used to join or immobilize a saccharide or a specificity domain. The saccharides and specificity domains can be joined to inorganic supports, such as silicon oxide material (e.g., silica gel, zeolite, diatomaceous earth or aminated glass) by, for example, a covalent linkage through a hydroxy, carboxy, or amino group and a reactive group on the support. In some embodiments, the support has a hydrophobic surface that interacts with a portion of the specificity domain and/or saccharide or saccharide conjugate (e.g., glycolipid) by a hydrophobic non-covalent interaction. In some cases, the hydrophobic surface of the support is a polymer such as plastic or any other polymer in which hydrophobic groups have been linked such as polystyrene, polyethylene or polyvinyl.

Additionally, supports such as proteins and oligo/polysaccarides (e.g., cellulose, starch, glycogen, chitosane or aminated sepharose) can be used by exploiting reactive groups on the specificity domains or saccharides, such as a hydroxy or an amino group, to join to a reactive group on the support so as to create the covalent bond. Still more supports containing other reactive groups that are chemically activated so as to attach the saccharides and specificity domains can be used (e.g., cyanogen bromide activated matrices, epoxy activated matrices, thio and thiopropyl gels, nitrophenyl chloroformate and N-hydroxy succinimide chlorformate linkages, or oxirane acrylic supports).

The insertion of linkers (e.g., "λ linkers" engineered to resemble the flexible regions of λ phage) of an appropriate length between the specificity domain and/or the plurality of saccharides and the support are also contemplated so as to encourage greater flexibility and overcome any steric hindrance that can be encountered. The determination of an appropriate length of linker that allows for optimal binding can be found by screening the attached molecule with varying linkers in the characterization assays detailed herein.

Preferred embodiments include specificity exchangers that comprise glycoconjugates and support-bound saccharides that are commonly referred to as glycoproteins, proteoglycans, glycopeptides, peptidoglycans, glyco-amino-acids, glycosyl-amino-acids, glycolipids, and related compounds. The glycoproteins that can be used with an embodiment described herein include compounds that contain a carbohydrate and a protein. The carbohydrate may be a monosaccharide, disaccharide(s), oligosaccharide(s), polysaccharide(s), their derivatives (e.g., sulfo- or phospho-substituted), and other similar compounds. There are two major classes of glycoproteins that can be used, O-linked glycans and the N-linked glycans. N-linked glycoproteins contain an N-acetylglucosamine residue linked to the amide nitrogen of an asparagine residue in the protein. The most common O-linkage involves a terminal N-acetylgalactosamine residue in the oligosaccharide linked to a serine or threonine residue of the protein. While specificity exchangers that comprise a glycoprotein can include one, a few, or many carbohydrate units, some embodiments comprise a proteoglycan, a subclass of glycoproteins that are polysaccharides that contain amino sugars.

The glycopeptides that can be used with some of the embodiments described herein include compounds having a carbohydrate linked to an oligopeptide composed of L- and/or D-amino acids. The peptidoglycans that can be used comprise a glycosaminoglycan formed by alternating residues of D-glucosamine and either muramic acid {2-amino-3-O—[(R)-1-carboxyethyl]-2-deoxy-D-glucose} or L-talosaminuronic acid (2-amino-2-deoxy-L-taluronic acid), which are usually N-acetylated or N-glycosylated.

The glyco-amino-acids that can be used with the embodiments described herein comprise a saccharide attached to a single amino acid, whereas the glycosyl-amino-acids that can be used include compounds comprising a saccharide linked through a glycosyl linkage (O—, N— or S—) to an amino acid. (The hyphens are used to avoid implying that the carbohydrate is necessarily linked to the amino group.) In some embodiments, the antigenic domain comprises a glycolipid, which is a compound comprising one or more monosaccharide residues bound by a glycosidic linkage to a hydrophobic moiety such as an acylglycerol, a sphingoid, a ceramide (N-acylsphingoid) or a prenyl phosphate, for example. Some of the specificity exchangers described herein can also comprise a glycoconjugate (e.g., lectins).

Preferred embodiments, however, include specificity exchangers that comprise human proteins or glycoconjugates that are commonly referred to as blood group antigens. These antigens are generally surface markers located on the outside of red blood cell membranes. Most of these surface markers are proteins, however, some are carbohydrates attached to lipids or proteins. Structurally, the blood group determinants that can be used with the embodiments described herein fall into two basic categories known as type I and type II. Type I comprises a backbone comprised of a galactose 1-3 β linked to N-acetyl glucosamine while type II comprises, instead, a 1-4 β linkage between the same building blocks (cf. N-acetyl lactosamine). The position and extent of a-fucosylation of these backbone structures gives rise to the Lewis-type and H-type specificities. Thus, monofucosylation at the $C_4$-hydroxyl of the N-acetyl glucosamine (Type I series) constitutes the $Le^a$ type, whereas fucosylation of the $C_3$-hydroxyl of this sugar (Type II series) constitutes the $Le^x$ determinant. Additional fucosylation of Le$^a$ and Le$^x$ types at the C$_2$,-hydroxyl of the galactose sector specifies the Le$^b$ and Le$^y$ types, respectively.

The presence of an a-monofucosyl branch, solely at the C$_2$,-hydroxyl in the galactose moiety in the backbone, constitutes the H-type specificty (Types I and II). Further permutation of the H-types by substitution of a-linked galactose or a-linked N-acetylgalactosamine at its ,-hydroxyl group provides the molecular basis of the familiar serological blood group classifications A, B, and O. (See e.g., Lowe, J. B., The Molecular Basis of Blood Diseases, Stamatoyannopoulos, et. al., eds., W. B. Saunders Co., Philadelphia, Pa., 1994, 293., herein expressly incorporated by reference in its entirety.)

By first determining a patient's particular set of blood group antigens, one can select a specificity exchanger comprising one or more blood group antigens that are outside of the repertoire of the patient so as to generate a potent response to the antigenic domain of the specificity exchanger in the patient and thereby redirect the antibodies present in the patient to the pathogen that is specific for the specificity domain of the specificity exchanger. Accordingly, specificity exchangers that are specific for several different pathogens can be made to have antigenic domains that comprise many different combinations of blood group antigens so that a potent immune response can be obtained in any particular individual. The next section describes the manufacture of specificity exchangers comprising saccharides and glycoconjugates, in particular blood group antigens, in greater detail.

Making Specificity Exchangers that Comprise Saccharides and Glycoconjugates

The manufacture of antigen/antibody specificity exchangers and ligand/receptor specificity exchangers has been described previously. (See e.g., U.S. Pat. Nos. 5,869,232; 6,040,137; 6,245,895; 6,417,324; 6,469,143; 6,660,842; 6,933,366; and U.S. Patent Publication No. 20020058247; U.S. application Ser. No. 09/664,025; and International App. Nos. PCT/SE95/00468 and PCT/IB01/00844, and PCT/IB01/02327, all of which are herein expressly incorporated by reference in their entireties). The manufacture of these specificity exchangers can be modified so as to join or incorporate saccharides and glycoconjugates according to methods that are known in the art.

Several issues merit consideration in contemplating the synthesis of such blood group substances and their neoglycoconjugates, however. For purposes of synthetic economy it is helpful to gain relief from elaborate protecting group manipulations common to traditional syntheses of complex branched carbohydrates. Another issue involves fashioning a determinant linked to a protein carrier. In crafting such constructs, it may be beneficial to incorporate appropriate spacer units between the carbohydrate determinant and the carrier. (See e.g., Stroud, M. R., et al., Biochemistry, 1994, 33, 10672; Yuen, C.-T., et al., J. Biochem., 1994, 269, 1595; and Stroud, M. R., et al., J. Biol. Chem., 1991, 266, 8439., all of which are herein expressly incorporated by reference in entirities)

TABLE 2 provides a non-exclusive list of blood group antigens that can be joined to or incorporated in a specificity exchanger.

TABLE 2

| | Blood group carrier or effector protein name system | Gene name | SWISS-PROT cross reference | Antigen names |
|---|---|---|---|---|
| ABO | Fucosylglycoprotein alpha-n-acetylgalactosaminyltransferase (EC 2.4.1.40) (Histo-blood group A transferase)/ Fucosylglycoprotein 3-alpha-galactosyltransferase (EC 2.4.1.37) (Histo-blood group B transferase) | Gene: ABO | BGAT_HUMAN (P16442) | Antigens: A/B |
| Chido/ Rodgers | Complement C4 | Gene: C4A and C4B | CO4_HUMAN (P01028) | Antigens: Ch1 to Ch6, WH, Rg1, Rg2 |
| Colton | Aquaporin-CHIP (Aquaporin 1). | Gene: AQP1; CHIP28 | AQP1_HUMAN (P29972) | Antigens: Co(a/b) |
| Cromer | Complement decay-accelerating factor (Antigen CD55). | Gene: DAF; CD55 | DAF_HUMAN (P08174) | Antigens: Cr(a), Dr(a), Es(a), Tc(a/b/c), Wd(a), WES(a/b), IFC, UMC |
| Diego | Band 3 anion transport protein (Anion exchange protein 1) (AE 1). | Gene: SLC4A1; AE1; EPB3 | B3AT_HUMAN (P02730) | Antigens: Di(a/b), Wr(a/b), Wd(a), Rb(a), WARR |
| Dombrock | Dombrock glycoprotein. | Gene: DO | Not yet identified | Antigens: Do(a/b), Gy(a), Hy, Jo(A) |
| Duffy | Duffy antigen (Fy glycoprotein) (Glycoprotein D) (GpFy). | Gene: FY; GPD; DARC | DUFF_HUMAN (Q16570) | Antigens: Fy(a/b) |
| Gerbich | Glycophorin C (PAS-2') (Glycoprotein beta) (Glycoconnectin) (Sialoglycoprotein D) (Glycophorin D) (GpD). | Gene: GYPC; GPC | GLPC_HUMAN (P04921) | Antigens: An(a), Dh(A), Ls(a), Wb |

TABLE 2-continued

| Blood group system | Blood group carrier or effector protein name | Gene name | SWISS-PROT cross reference | Antigen names |
|---|---|---|---|---|
| Hh | Galactoside 2-L-fucosyltransferase 1 (EC 2.4.1.69) (Alpha(1,2)Ft 1) (Fucosyltransferase 1). | Gene: FUT1 | FUT1_HUMAN (P19526) | |
| | Galactoside 2-L-fucosyltransferase 2 (EC 2.4.1.69) (Alpha(1,2)Ft 2) (Fucosyltransferase 2) (Secretor factor). | Gene: FUT2 | FUT2_HUMAN (Q10981) | Antigens: H/h, Se/se |
| Indian | CD44 antigen (Phagocytic glycoprotein I) (PGP-1) (Hutch-I) (Extracellular matrix receptor-III) (ECMR-III) (Hermes antigen) (Hyaluronate receptor) (Heparan sulfate proteoglycan) (Epican). | Gene: CD44; LHR | CD44_HUMAN (P16070) | Antigens: In(a/b) |
| Kell | Kell blood group glycoprotein (EC 3.4.24.-). | Gene: KEL | KELL_HUMAN (P23276) | Antigens: K/k, Kp(a/b/c), Js(a/b), Ul(a), KEL11/17, KEL14/24 |
| Kidd | Urea transporter, erythrocyte. | Gene: SLC14A1; UT1; HUT11; UTE; JK; RACH1 | UT1_HUMAN (Q13336) | Antigens: Jk(a/b) |
| Knops | Complement receptor type 1 (C3b/C4b receptor) (Antigen CD35). | Gene: CR1; C3BR | CR1_HUMAN (P17927) | Antigens: Kn(a/b), McC(a), Sl(a), Yk(a) |
| Kx | Membrane transport protein XK (Kx antigen). | Gene: XK | XK_HUMAN (P51811) | |
| Landsteiner-Wiener | Landsteiner-Wiener blood group glycoprotein. | Gene: LW | LW_HUMAN (Q14773) | Antigens: Lw(a/b) |
| Lewis | Galactoside 3(4)-L-fucosyltransferase (EC 2.4.1.65) (Fucosyltransferase 3) (FUCT-III). | Gene: FUT3; LE | FUT3_HUMAN (P21217) | Antigens: Le(a/b) |
| Lutheran | Lutheran blood group glycoprotein (B-CAM cell surface glycoprotein) (Auberger B antigen) (F8/G253 antigen). | Gene: LU; BCAM; MSK19 | LU_HUMAN (P50895) | Antigens: Lu(a/b), Au(a/b), LU6 to LU20 |
| MNS | Glycophorin A (PAS-2) (Sialoglycoprotein alpha) (MN sialoglycoprotein). | Gene: GYPA; GPA | GLPA_HUMAN (P02724) | Antigens: M/N, S/s, U, He, Mi(a), M(c), Vw, Mur, M(g), Vr, M(e), Mt(a), St(a), Ri(a), Cl(a), Ny(a), Hut, Hil, M(v), Far, Mit, Dantu, Hop, Nob, En(a), ENKT, etc. |
| | Glycophorin B (PAS-3) (Sialoglycoprotein delta) (SS-active sialoglycoprotein). | Gene: GYPB; GPB | GLPB_HUMAN (P06028) | |
| P | A yet undefined galactoyltransferase. | Gene: P1 | Not yet identified | Antigens: P1 |
| Rh | Blood group RH(CE) polypeptide (Rhesus C/E antigens) (RHPI). | Gene: RHCE; RHC; RHE | RHCE_HUMAN (P18577) | Antigens: C/c, E/e, D, f, C(e), C(w), C(x), V, E(w), G, Tar, VS, D(w), cE, etc. |
| | Blood group RH(D) polypeptide (Rhesus D antigen) (RHPII). | Gene: RHD | RHD_HUMAN (Q02161) | |
| Scianna | Scianna glycoprotein. | Gene: SA | Not yet identified | Antigens: Sc(1/2), Sc3 |
| Xg | Xg glycoprotein (Protein PBDX). | Gene: XG; PBDX | XG_HUMAN (P55808) | Antigens: Xg(a) |
| Yt | Acetylcholinesterase (EC 3.1.1.7). | Gene: ACHE | ACES_HUMAN (P22303) | Antigens: Yt(a/b) |

Additional blood groups can include Lewis$^x$-BSA, 2'-Fucosyllactose-BSA (2'FL-BSA), Lacto-N-fucopentaose II-BSA, Lacto-N-fucopentaose III-BSA, Lacto-N-fucopentaose I-BSA (LNFPI-BSA), Lacto-N-difucohexaose I-BSA (LNDFHI-BSA), Blood Group A-BSA, Blood Group B-BSA, Globotriose-HSA, Gala1-4Galb1-4Glc-HSA, and the like.

While blood group antigens have been discussed in detail, it is important to point out that any saccharide or glycoconjugate can be included in the antigenic domain of the specificity exchangers described herein. Antigenic saccharides and glycoconjugates are well known in the art and are readily available from a commercial supplier such as V-Labs, Inc. (Covington, La.). Saccharides and glycoconjugates can also be synthesized using conventional techniques (as will be described in more detail). Potential saccharides and glycoconjugates that can be used herein can be derived from pathogens, including bacteria, viruses (e.g., L, M, and S glycoproteins from HBV, and gp160, gp120 and gp41 from HIV), protozoan, and fungi, cancer cells, toxins, cells affected by autoimmune diseases such as lupus, multiple sclerosis, rheumatoid arthritis, diabetes, psoriasis, Graves disease and the like.

Specific core structure neoglycoproteins that can be used in the antigenic domains described herein include: N-Acetyllactosamine-BSA (3-atom spacer), N-Acetyllactosamine-BSA (14-atom spacer), α1-3,α1-6 Mannotriose-BSA (14-atom spacer) and the like. Monosaccharide neoglycoproteins that can be used in the antigenic domains described herein include: N-Acetylglucosamine-BSA (14-atom spacer), N-Acetylgalactosamine-BSA (14-atom spacer), and the like. Tumor antigen neoglycoproteins that can be used in the antigenic domains described herein include: T-Antigen-HSA Galβ1-3GalNAc-HSA (3-atom spacer), Tn-Antigen-HSA GalNAca1-O-(Ser-N-Ac-CO)-Spacer-NH-HSA, and the like. Sialyated neoglycoproteins that can be used in the antigenic domains described herein include: 3' Sialyl-N-acetyllactosamine-BSA (3-atom spacer), 3'-Sialyl-N-acetyllactosamine-BSA (14-atom spacer), 3'-Sialyl Lewis$^x$-BSA (3-atom spacer), 3'-Sialyl Lewis$^x$-HSA (3-atom spacer), 3'-Sialyl-3-Fucosyl-Lactose-BSA (3-atom spacer), 3'-Sialyl Lewis$^x$-BSA (14-atom spacer), and the like.

In certain embodiments, the antigenic domain can include Gal α (1,3) Gal β(gal antigen), a carbohydrate antigen. The gal antigen is produced in large amounts on the cells of pigs, mice and New World monkeys by the glycosylation enzyme galactosyltransferase (α(1,3)GT). Galactosyltransferase is active in the Golgi apparatus of cells and transfers galactose from the sugar-donor uridine diphosphate galactose (UDP-galactose) to the acceptor N-acetyllactosamine residue on carbohydrate chains of glycolipids and glycoproteins, to form gal antigen.

The gal antigen is completely absent in humans, apes and Old World monkeys because their genes encoding α (1,3) GT have become inactivated in the course of evolution. (Xing et al., 01-2-xl *Cell Research* 11(2): 116-124 (2001), herein expressly incorporated by reference in its entirety.) Since humans and Old World primates lack the gal antigen, they are not immunotolerant to it and produce anti-gal antigen antibodies (anti-Gal) throughout life in response to antigenic stimulation by gastrointestinal bacteria. (Id.) It has been estimated that as many as 1% of circulating B cells are capable of producing these antibodies. (Id.) The binding of anti-Gal to gal antigens expressed on glycolipids and glycoproteins on the surface of endothelial cells in donor organs leads to activation of the complement cascade and hyperacute rejection, and also plays an important role in occurrence of complement-independent delayed xenograft rejection. (Id.) Accordingly, the gal antigen has the ability to generate a potent immune response.

In certain embodiments the gal antigen to be joined or incorporated into a specificity exchanger is selected from gal α (1,3) gal series neoglycoproteins and can include: Gala1-3Gal-BSA (3-atom spacer), Gala1-3Gal-BSA (14-atom spacer), Gala1-3Gal-HSA (3-atom spacer), Gala1-3Gal-HSA (14-atom spacer), Gala1-3Galβ1-4GlcNAc-BSA (3-atom spacer), Gala1-3Galβ1-4GlcNAc-BSA (14-atom spacer), Gala1-3Galβ1-4GlcNAc-HSA (3-atom spacer), Gala1-3Galβ1-4GlcNAc-HSA (14-atom spacer), Galili Pentasaccharide-BSA (3-atom spacer), and the like. In other embodiments the gal antigen can be selected from gal α(1,3) gal analogue neoglycoproteins, including Gala1-3Galβ1-4Glc-BSA (3-atom spacer), Gala1-3Galβ1-4Glc-HSA (3-atom spacer), Gala1-3Galβ1-3GlcNAc-BSA (3-atom spacer), Gala1-3Galβ1-3GlcNAc-HSA (3-atom spacer), Gala1-3Galβ1-4(3 -deoxyGlcNAc)-HSA (3-atom spacer), Gala1-3Galβ1-4(6-deoxyGlcNAc)-HSA, and the like.

Danishefsky, et al., discloses several antigenic saccharides and glycoconjugates, and methods of synthesizing said compounds. (See U.S. Pat. No. 6,303,120, herein expressly incorporated by reference in its entirety). Specifically, this patent provides a method of synthesizing Le$^y$-related antigens as well as artificial protein-conjugates of the oligosaccharide. In certain embodiments, these antigens contain a novel array of features including the α-linkage between the B and the C entities, as well as the β-linked ring D gal-NAc residue. (For the synthesis of a related structure (SSEA-3), which lacks the fucose residue see: Nunomura, S.; Ogawa, T., Tetrahedron Lett., 1988, 29, 5681-5684., herein expressly incorporated by reference in its entirety.) In general, the methods described in U.S. Pat. No. 6,303,120, herein expressly incorporated by reference in its entirety can be used or modified so as to join or incorporate the saccharides or glycoconjugates described herein with a specificity exchanger.

A major obstacle in the field of glycobiology is access to pure, chemically well defined complex carbohydrates and glycoconjugates. (See Randell, Karla D., et al., High-throughput Chemistry toward Complex Carbohydrates and Carbohydrate-like Compounds, *National Research Council of Canada*, publication no. 43876, Feb. 13, 2001, herein expressly incorporated by reference in its entirety). Unlike nucleic acids and polypeptides, these are non-linear molecules and the carbohydrate moieties present tremendous challenges in developing their total syntheses. (Id.) These polyhydroxy compounds contain an array of monosaccharide units and have a variety of glycosidic linkages between them. (Id.) Each glycosidic linkage can exist in the α- or β-anomeric configuration. (Id.) Therefore, carbohydrate syntheses can require many orthogonal protection-deprotection schemes and involve difficult glycosyl coupling reactions. (Id.) Recently, efforts have been made to develop automated syntheses of complex carbohydrates. (Id.)

While vastly more complicated than the techniques for synthesizing polynucleotides and polypeptides, techniques for synthesizing saccharides and glycoconjugates are known in the art. These techniques are discussed in the sections that follow as they fall into enzyme-based approaches, cell-based approaches, and chemical synthesis-based approaches.

Enzyme Synthesis

Different methods for synthesizing saccharides and glycoconjugates described herein can be found in U.S. Pat. No. 6,046,040, issued to Nishiguchi et al. (2000), which is hereby expressly incorporated by reference in its entirety. Specifically this patent discloses using enzyme-catalyzed in vitro reactions to synthesize saccharides and glycoconjugates. See also Toone et al., *Tetrahedron Reports* (1990) (45)17:5365-5422. Enzymatic approaches have been gaining popularity for the synthesis of saccharides and glycoconjugates in part because enzymes feature exquisite stereo- and regioselectivity and catalyze the reaction under very mild conditions. Extensive protection-deprotection schemes are thus unnecessary, and the control of anomeric configuration is simplified.

To produce some of the specificity exchangers described herein, the following enzymes may be used: saccarglycosyltransferases, glycosidases, glycosyl hydrolases or glycosyltransferases. Glycosyltransferases regulate the biosynthesis of carbohydrate antigens in cells and are responsible for the addition of carbohydrates to the oligosaccharide chain on glycolipids and glycoproteins in a sequential manner. Glycosyltransferases catalyze the addition of activated sugars, in a stepwise fashion, to a protein or lipid or to the non-reducing end of a growing oligosaccharide. Typically a relatively large number of glycosyltransferases are used to synthesize carbohydrates. Each NDP-sugar residue requires a distinct class of glycosyltransferase and each of the more than one hundred glycosyltransferases identified to date appears to catalyze the formation of a unique glycosidic linkage.

According to one enzyme-catalsyed method of synthesis, saccharides are synthesized using a solid phase method that utilizes glycal (Danishefsky et al., *Science*, 260, 1307 (1993)). This method includes (i) binding a glycal to a polystyrene-divinylbenzene copolymer via a diphenylsilyl group to allow reaction between the glycal and 3,3-dimethyldioxirane, that converts glycal to a 1,2-anhydrosugar, and (ii) using this anhydrosugar as a sugar donor, reaction with a different glycal suitably protected to form a glycoside glycal, and these steps are repeated. According to this method, a new glycosidic linkage is stereoselectively formed.

A solid phase method of sugar chain synthesis can also be used to generate saccharides or glycoconjugates to be used in the specificity exchangers described herein. This method utilizes glycosyltransferase, which is capable of stereoselectively forming a glycosidic linkage without any protection. In the past, this method has not reached its potential due to the fact that available glycosyltransferase is limited in kind and is expensive. In recent years, however, genes of various glycosyltransferases have been isolated and a large-scale production of glycosyltransferase by genetic techniques is common place.

U. Zehavi et al. reports a solid phase synthesis method that can be used to manufacture some of the specificity exchangers described herein, whereby a glycosyltransferase and a polyacrylamide gel bound with an aminohexyl group on a solid phase carrier is used. (See *Carbohydr. Res.*, 124, 23 (1983), *Carbohydr. Res.*, 228, 255 (1992), hereby expressly incorporated by reference in its entirety). This method comprises the steps of converting a suitable monosaccharide to 4-carboxy-2-nitrobenzylglycoside, condensing this glycoside with the amino group of the above-mentioned carrier, elongating the sugar chain by glycosyltransferase using the condensate as a primer, and releasing the oligosaccharide by photolysis.

In the past, there was a common understanding that glycosyltransferase does not react well with saccharide or oligosaccharide bound to a solid phase carrier, and that efficient elongation of a sugar chain is difficult to achieve. However, more recently it has been discovered that the linkage between 4-carboxy-2-nitrobenzylglycoside and solid phase carrier by a linker having a long chain, such as hexamethylene and octamethylene, improved sugar transfer yield at the maximum of 51% (*React. Polym.*, 22, 171 (1994), *Carbohydr. Res.*, 265, 161 (1994)).

C. H. Wong et al. report a method of enzymatic synthesis whereby glycosyltransferase is used to elongate sugar residues bound to aminated silica and, once complete, the elongated sugar chain is cleaved from the support using α-chymotrypsin. (See *J. Am. Chem. Soc.*, 116, 1136 (1994), which is hereby expressly incorporated by reference in its entirety). By this method, the transglycosylation yield was 55%. Similarly, M. Meldal et al. reports another method of elongating a sugar chain using glycosyltransferase and a polymer of mono- and diacryloyl compound of diaminated poly(ethylene glycol) as a primer. The sugar chain was released by trifluoroacetic acid. (See *J. Chem. Soc., Chem. Commun.*, 1849 (1994), which is hereby expressly incorporated by reference in its entirety). As mentioned above, when a sugar chain is elongated by glycosyltransferase on a solid phase carrier, the kind of group (linker) that connects the solid phase carrier to the sugar residue (receptor of initial transglycosylation) varies transglycosylation yield. When the sugar chain is liberated from the carrier, the presence of a specifically cleavable bond in the linker is desired. In sugar chain elongation by glycosyltransferase, the use of an immobilized glycosyltransferase that permits repetitive use is also desired. Preferably, if an immobilized glycosyltransferase is used for sugar chain elongation, the reaction is carried out on a water soluble carrier.

U.S. Pat. No. 6,046,040, issued to Nishiguchi et al. (2000), which is hereby expressly incorporated by reference in its entirety, describes sugar chain synthesis using an immobilized glycosyltransferase and a water soluble carrier. Accordingly, by one approach to generate the sugar-containing antigenic domains described herein, the following steps can be employed: (i) binding a sugar residue to the side chain of a water-soluble polymer via a linker having a selectively cleavable linkage to give a primer, and bringing said primer into contact with an immobilized glycosyltransferase in the presence of a sugar nucleotide, to transfer a sugar residue of said sugar nucleotide to the sugar residue of said primer, (ii) elongating a sugar chain by transfer of plural sugar residues by repeating the step (i) at least once, (iii) removing, where necessary, a by-produced nucleotide or an unreacted sugar nucleotide, and (iv) repeating the steps (i)-(iii) where necessary and releasing the sugar chain by selectively cleaving the cleavable linkage in the linker, from the above-mentioned primer connecting the sugar chain elongated by the transfer of plural sugar residues. The methods disclosed in U.S. Pat. No. 6,046,040 can be used to synthesize glycoconjugates having an optional sugar chain structure, such as oligosaccharides, glycopeptides and glycolipids, as well. The application of enzymes to an automated scheme of saccharide or glycoconjugate synthesis is also possible. Both solution and solid-phase methods can be used for automated synthesis.

In some embodiments, an apparatus that utilize enzymes to synthesize saccharides and glycoconjugates can be used herein. U.S. Pat. No. 5,583,042, which is hereby expressly incorporated by reference in its entirety, for example, describes an apparatus that utilizes combinations of glycosyltransferases, for the synthesis of specific saccharides and glycoconjugates. The next section describes several cell-based approaches to manufacture specificity exchangers comprising saccharides or glycoconjugates.

Cell Based Synthesis

In addition to using in vitro enzyme catalyzed reactions, any available cell-based methods can be used to synthesize the saccharides and glycoconjugates described herein. U.S. Pat. No. 6,458,937, which is hereby expressly incorporated by reference in its entirety, describes several cell based protocols for synthesizing saccharides and glycoconjugates. By one approach to synthesize the specificity exchangers described herein saccharides and glycoconjugates are first made by (a) contacting a cell with a first monosaccharide, and (b) incubating the cell under conditions whereby the cell (i) internalizes the first monosaccharide, (ii) biochemically processes the first monosaccharide into a second saccharide, (iii) conjugates the saccharide to a carrier to form a glycoconjugate, and (iv) extracellularly express the glycoconjugate to form an extracellular glycoconjugate comprising a selectively reactive functional group. By then reacting the glycoconjugate containing the functional group with a specificity exchanger comprising a reactive functional group, the glycoconjugate and specificity exchanger are joined. Subject compositions can include cyto-compatible monosaccharides comprising a nitrogen or ether linked functional group, for example, that are selectively reactive with similar groups present on a specificity exchanger.

By another approach, the saccharides and glycoconjugates can be synthesized by a) contacting a cell with a first monosaccharide comprising a first functional group, and b) incubating the cell under conditions whereby the cell (i) internalizes the first monosaccharide, (ii) biochemically processes the first monosaccharide into a second monosaccharide which comprises a second functional group, (iii) conjugates the second monosaccharide to a carrier to form a glycoconjugate comprising a third functional group, and (iv) extracellularly expresses the glycoconjugate to form an extracellular glycoconjugate comprising a fourth, selectively reactive, functional group.

Extracellular glycoconjugates synthesized by the above method may be presented in multiple forms such as membrane-associated (e.g., a membrane bound glycolipid or glycoprotein), associated with cell-proximate structures (e.g., extracellular matrix components or neighboring cells), or in a surrounding medium or fluid (e.g., as a secreted glycoprotein). The selective reactivity of the fourth functional group permits selective targeting of the glycoconjugate as presented by the cell. For example, fourth functional groups of surface associated glycoconjugates can provide a reactivity that permits the selective targeting of the glycoconjugate in the context of the associated region of the cell surface. Preferentially reactivity may be affected by a more reactive context. For example, the glycoconjugate-associated fourth functional group provides greater accessibility, greater frequency or enhanced reactivity as compared with such functional groups present proximate to the site of, but not associated with the glycoconjugate. In a preferred embodiment, the fourth functional group is unique to the region of glycoconjugate presentation.

The selective reactivity provided by the fourth functional group may take a variety of forms including nuclear reactivity, such as the neutron reactivity of a boron atom, and chemical reactivity, including covalent and non-covalent binding reactivity. In any event, the fourth functional group should be sufficient for the requisite selective reactivity. A wide variety of chemical reactivities may be exploited to provide selectivity, depending on the context of presentation. For example, fourth functional groups applicable to cell surface-associated glycoconjugates include covalently reactive groups not normally accessible at the cell-surface, including alkenes, alkynes, dienes, thiols, phosphines and ketones. Suitable non-covalently reactive groups include haptens, such as biotin, and antigens such as dinitrophenol.

In more embodiments, the nature of the expressed glycoconjugate is a function of the first monosaccharide, the cell type and incubation conditions. In these embodiments, the resident biochemical pathways of the cell act to biochemically process the first monosaccharide into the second monosaccharide, conjugate the second monosaccharide to an intracellular carrier, such as an oligo/polysaccharide, lipid or protein, and extracellularly express the final glycoconjugate. Alternatively, the expressed glycoconjugate may also be a function of further manipulation. For example, the fourth functional group may result from modifying the third functional group as initially expressed by the cell. For example, the third functional group may comprise a latent, masked or blocked group that requires a post-expression treatment, e.g., chemical cleavage or activation, in order to generate the fourth functional group. Such treatment may be effected by enzymes endogenous to the cell or by exogenous manipulation. Hence, the third and fourth functional groups may be the same or different, depending on cellular or extracellular processing events.

As indicated, a functional group can be a masked, latent, inchoate or nascent form of another functional group. Examples of masked or protected functional groups and their unmasked counterparts are provided in TABLE 3. Masking groups may be liberated in any convenient way; for example, ketal or enols ether may be converted to corresponding ketones by low pH facilitated hydrolysis. Alternatively, many specific enzymes are known to cleave specific protecting groups, thereby unmasking a functional group.

TABLE 3

| Masking group | Unmasked group |
| --- | --- |
| dialkyl ketal | ketone |
| acetal | aldehyde |
| enol ether | ketone or aldehyde |
| oxime | ketone |
| hydrazone | ketone |
| thioester | thiol |
| cobalt-complexed alkyne | alkyne |

In contrast, the nature of the intracellular glycoconjugate (comprising the third functional group) is generally solely a function of the first monosaccharide, the cell type and incubation conditions. For example, the first and second monosaccharides and the saccharide moiety incorporated into the intracellular glycoconjugate (as well as the first, second and third functional groups) may be the same or different depending on cellular processing events. For example, the first monosaccharide or functional group, cell and conditions may interact to form a chemically distinct second monosaccharide or functional group, respectively. For example, many biochemical pathways are known to interconvert monosaccharides and/or chemically transform various functional groups. Hence, predetermined interconversions are provided by a first monosaccharide, cell and incubation condition selection.

The first monosaccharide is selected to exploit permissive biochemical pathways of the cell to effect expression of the extracellular glycoconjugate. For example, many pathways of sialic acid biosynthesis are shown to be permissive to a wide variety of mannose and glucose derivatives. The first functional group may be incorporated into the first monosaccharide in a variety of ways. In preferred embodiments, the functional group is nitrogen or ether linked.

A wide variety of cells may be used according to the disclosed methods including eukaryotic, especially mammalian cells (e.g., pigs, mice, and New World monkeys) and prokaryotic cells. The cells may be in culture, e.g., immortalized or primary cultures, or in situ, e.g., resident in the organism.

The methods herein are also directed to forming products attached to the cell. Generally, these methods involve expressing an extracellular glycoconjugate as described above wherein the expressed glycoconjugate is retained proximate to the cell; for example, by being bound to membrane or extracellular matrix components. Then the fourth functional group is contacted with an agent which selectively reacts with the fourth functional group to form a product.

A wide variety of agents may be used to generate a wide variety of products. Generally, agent selection is dictated by the nature of the fourth functional group and the desired product. For example, with chemically reactive fourth functional groups, the agent provides a fifth functional group that selectively chemically reacts with the fourth functional group. For example, where the fourth functional group is a ketone, suitable fifth functional groups include hydrazines, hydroxylamines, acyl hydrazides, thiosemicarbazides and beta-aminothiols. In other embodiments, the fifth functional group is a selective noncovalent binding group, such as an antibody idiotope. In yet other embodiments, suitable agents include radioactivity such as alpha particles which selectively react with fourth functional groups comprising radiosensitizers such as boron atoms; oxidizers such as oxygen which react with fourth functional groups comprising a surface metal complex, e.g., to produce cytotoxic oxidative species; etc. Alternatively, a functional group on the cell surface might have unique properties that do not require the addition of an external agent (e.g., a heavy metal which serves as a label for detection by electron microscopy). Further examples of products formed by the interaction of a cell surface functional group and an agent are given in TABLE 4.

TABLE 4

| Functional group | Agent | Product |
| --- | --- | --- |
| ketone | hydrazide | hydrazone |
| diene | dienophile | Diels-Alder adduct |
| thiol | alpha-bromo amide | thioether |
| boron | neutrons | radiation |
| biotin | avidin | biotin-avidin complex |
| dinitrophenol (DNP) | anti-DNP antibodies | DNP-antibody complex |
| Fluorescein | UV light | green light |
| iron complex | oxygen | peroxy radicals |

Frequently, the agent comprises an activator moiety, which provides a desired activity at the cell. A wide variety of activator moieties may be used, including moieties which alter the physiology of the cell or surrounding cells, label the cell, sensitize the cell to environmental stimuli, alter the susceptibility of the cell to pathogens or genetic transfection, etc. Exemplary activator moieties include toxins, drugs, detectable labels, genetic vectors, molecular receptors, and chelators.

A wide variety of compositions useful in the disclosed methods are provided herein. These compositions include cyto-compatible monosaccharides comprising a functional group, preferably a nitrogen or ether linked functional group, which group is selectively reactive at a cell surface. Exemplary functional groups of such compounds include alkynes, dienes, thiols, phosphines, boron and, especially, ketones. The term substituted or unsubstituted alkyl is intended to encompass alkoxy, cycloalkyl, heteroalkyl, and similar compounds. Similarly, the term substituted or unsubstituted aryl is intended to encompass aryloxy, arylalkyl (including arylalkoxy, etc.), heteroaryl, arylalkynyl, and similar compounds. The term substituted or unsubstituted alkenyl is intended to analogously encompass cycloalkenyl, heteroalkenyl, etc. Analogous derivatives are made with other monosaccharides having permissive pathways of bioincorporation. Such monosaccharides are readily identified in convenient cell and protein-based screens, such as described below. For example, functionalized monosaccharides incorporated into cell surface glycoconjugates can be detected using fluorescent labels bearing a complementary reactive functional group. A cell-based assay suitable for mechanized high-throughput optical readings involves detecting ketone-bearing monosaccharides on cell surfaces by reaction with biotin hydrazide, followed by incubation with FITC-labeled avidin and then quantitating the presence of the fluorescent marker on the cell surface by automated flow cytometry. A convenient protein-based screen involves isolating the glycoconjugate (e.g., gel blots), affinity immobilization, and detecting with the complementary reactive probe (e.g., detone-bearing glycoconjugates detected with biotin hydrazide), followed by incubation with avidin-alkaline phosphatase or avidin-horseradish peroxidase. Alternatively, monosaccharides bearing unusual functional groups can also be detected by hydrolysis of the glycoconjugate followed by automated HPLC analysis of the monosaccharides. The following section describes several approaches to manufacture the specificity exchangers described herein that utilize methods of chemical synthesis.

Chemical Synthesis

In addition to using enzyme catalyzed methods and cell-based methods, the specificity exchangers comprising saccharides and glycoproteins can be made using methods directed to chemical synthesis. Examples of methods used to synthesize saccharides and glycoconjugates can be found in Pamela Sears et al., Toward Automated Synthesis of Oligosaccharides and Glycoproteins, *Carbohydrates and Glycobiology* 291 Science 2344 (Mar. 23, 2001), which is hereby incorporated by reference in its entirety. Most methods of chemical synthesis involve the activation of the anomeric leaving group with a Lewis acid. The Koenigs-Knorr method of coupling glycosyl halides, one of the first techniques to gain widespread usage, is still in common use, and most other glycosidation reagents used to date proceed by the same basic mechanism.

Chemical synthesis of saccharides and glycoconjugates can also be performed automatically. Generally for automated synthesis, it is convenient for the reactions to be performed on solid phase. This approach allows the rapid removal of reactants, relatively easy purifications, and (in the case of library construction) the encoding of the product either by position (as in a two-dimensional array "chip" format) or, for "mix and split" type library construction, by an accessory encoding reaction, in which the labels are added to the solid support as the chain is extended or by radio frequency-encoded combinatorial chemistry technology. Hydrophilic supports, such as polyethylene glycol-based resins, have been used with good success, as have "hybrid" resins, such as Tentagel, that have a polystyrene core coated in polyethylene. To a lesser extent, soluble supports, such as polyethylene glycols and derivatives, have been used in saccharide synthesis.

Another approach that can be used for saccharide and glycoconjugate synthesis is a one-pot reaction. One-pot reactions rely on the reactivity profile of different protected sugars to determine the synthesized product. The reactivity of a sugar is highly dependent on the protecting groups and the anomeric activating group used. By adding substrates in sequence from the most reactive to least reactive, one can assure the predominance of a desired target compound. The key to this approach is to have extensive quantitative data regarding the relative reactivities of different protected sugars, which is currently being generated by those with skill in the art of glycomics. These reactions are typically performed in solution, but in order to facilitate removal of reactants at the end, the final acceptor may be attached to a solid phase.

This approach can be made even more efficient through automation, such as a computer program. Compared with stepwise solid-phase synthesis, the one-pot approach uses protecting-group manipulation only at the stage of building block synthesis and thus holds greater potential for automation and for greater diversity of oligosaccharide structures.

Additionally, several other methodologies can be employed to synthesize the glycopeptides and glycoproteins that are joined to or incorporated in the specificity exchangers described herein. Several of these methods are discussed in Pamela Sears et al., Toward Automated Synthesis of Oligosaccharides and Glycoproteins, *Carbohydrates and Glycobiology* 291 Science 2344 (Mar. 23, 2001), which is hereby incorporated by reference in its entirety. By one approach, for example, attachment of saccharide chains to the specificity exchangers described herein is accomplished in a stepwise fashion, beginning from the nonreducing end and proceeding to the reducing end. As is the case with glycal-based synthetic schemes and the one-pot strategy outlined above, the ultimate acceptor can be an amino acid, peptide or glycopeptide. For coupling to hydroxylated amino acids, such as serine or threonine, the chemistry is very much the same as that used to construct the glycosidic bonds: the activated anomeric position is directly attacked by a deprotected hydroxyl group on the peptide. In the case of $NH_2$-linked glycosides, the reducing-end sugar is typically prepared first as a sugar azide, which is then reduced and coupled to a free aspartate via carbodiimide activation. The acceptor can be an amino acid, for which the product can be incorporated into solid-phase peptide synthesis (SPPS) schemes to produce the target glycopeptide, or it may itself be the final polypeptide. Glycosylated amino acids bearing typically one to three sugars have been used successfully in solid phase synthesis of many glycopeptides.

In certain embodiments the glycopeptide containing specificity exchangers described herein can be synthesized by glycosylating the peptide in a stepwise fashion from the reducing to the nonreducing end through chemical or enzymatic methods. Typically, a single glycosylated peptide is made by SSPS, the sugar is selectively deprotected, and the oligosaccharide is built up in a stepwise fashion. The singly glycosylated peptide can be constructed via SPPS, and the sugar can be completely deprotected to provide the substrate for the action of three successive glycosyltransferases. The synthesis of these glycopeptides can also be automated.

Extension of glycosylated peptides into glycoproteins can also be accomplished by a number of approaches. Workers (Allen, P. Z., and Goldstein, I. *J. Biochemistry,* 1967, 6, 3029; Rude, E., and Delius, M. M., *Carbohydr. Res.,* 1968, 8, 219; Himmelspach, K., et al., *Eur. J. Immunol.,* 1971, 1, 106; Fielder, R. J., et al., *J. Immunol.,* 1970, 105, 265) developed several techniques for conjugation of carbohydrates to protein carriers, for example. Most of them suffered by introducing an antigenic determinant in the linker itself, resulting in generation of polyclonal antibodies. Kabat (Arakatsu, Y., et al., *J. Immunol.,* 1966, 97, 858), and Gray (Gray, G. R., *Arch. Biochem. Biophys.* 1974, 163, 426) developed conjugation methods that relied on oxidative or reductive coupling, respectively, of free reducing oligosaccharides. The main disadvantage of these techniques, however, is that the integrity of the reducing end of the oligosaccharide was compromised. In 1975 Lemieux described the use an 8-carbomethoxy-1-octanol linker (Lemieux, R. U., et al., *J. Am. Chem. Soc.,* 1975, 97, 4076) which alleviated the problem of linker antigenicity and left the entire oligosaccharide intact. Equally effective in producing glycoconjugates was the allyl glycoside method described by Bernstein and Hall. (Bernstein, M. A., and Hall, L. D., *Carbohydr. Res.,* 1980, 78, C1.) In this technique the allyl glycoside of the deblocked sugar is ozonized followed by a reductive workup. The resultant aldehyde is then reductively coupled to a protein carrier with sodium cyanoborohydride.

Short peptides can also be coupled to larger ones by "native peptide ligation" strategies. Easier approaches to glycoprotein synthesis can be achieved through cell based methods, however. The glycans produced by this method will be determined by many factors, including the local protein structure around the glycosylation site and the relative amounts of glyco-processing enzymes produced in the cell. Many of these factors also vary with the cell line, so a glycoprotein produced in one cell line may have different glycosylation than the same protein produced in another cell line.

The resulting products however can be used as a starting point for many schemes in which the sugar chain is digested down to a simple homogeneous core and then reelaborated enzymatically. For example, N-glycosylated proteins can have the glycans digested down to the innermost N-acetylglucosamine by using endoglycosidases, thus converting a heterogeneous population to a homogeneous one in which each glycosylation site has only a single sugar attached. These simple glycoproteins can then be elaborated enzymatically to increase the size and complexity of the glycan by using glycosyltransferases or endoglycosidase-catalyzed transglycosylation. The transglycosidase approach is limited by the substrate specificity of the endoglycosidases, which are enzymes that cleave between the innermost N-acetylglucosamine residues of $N_2$-linked oligosaccharides. In certain embodiments the endoglycosidase can be endoglycosidase M from *Mucor hiemalis*, which accepts a wide range of high-mannose-, hybrid- and complex-type glycans.

Another option is to remove the glycosylated sections by using proteases and then reattach short, chemically synthesized glycopeptides in their place. This ligation can be accomplished enzymatically through the use of proteases or inteins, self-splicing polypeptides that are able to excise themselves from proteins posttranslationally. In the latter case, the peptide segment to be replaced is substituted at the genetic level with the sequence encoding the intein.

Proteases can catalyze peptide synthesis using either the thermodynamic approach or the kinetic approach. In the thermodynamic approach, peptides are condensed to form the larger product typically by precipitation of the product or by conducting the reaction in a solvent with low water activity. A more useful approach, as far as enzyme activity, stability, and solubility are concerned, is the kinetic approach, in which a peptide ester undergoes a competition between hydrolysis and aminolysis. The ratio of aminolysis to hydrolysis can be improved by adding an organic cosolvent to lower the water concentration and suppress amine ionization, by increasing the amine nucleophile concentration, or by modifying the enzyme active site. With regard to enzyme modification, the conversion of the active-site serine of serine proteases to a cysteine has been shown to be highly effective for creating a peptide ligase. Glycosylation of proteins has long been known to render them less susceptible to protease activity, and so it might be inferred that glycopeptides would be difficult to couple using proteases. A systematic study of subtilisin-catalyzed synthesis of glycopeptides, however, reveals that the protease could couple glycopeptides successfully, provided that the glycosylation site was not at the forming bond and that the coupling yields improved as the glycosylation site was placed farther away from it. One of the most effective and practical glycopeptide ester leaving groups is the benzyl-type ester generated from a modified Rink amide resin and cleaved with trifluoroacetic acid.

An alternate approach is to use intein-mediated coupling of glycopeptides to larger proteins. It is possible to intervene in the natural splicing reaction by removing the COOH-terminal extein, then allowing the reaction to be completed with an exogenously added nucleophile, which may be a glycopeptide. As in the native peptide ligation strategy, the peptide preferably contains a cysteine at the $NH_2$-terminus.

Glycoprotein purification procedures can be very similar to the purification of unglycosylated proteins. The first step in glycoprotein purification is usually to solublize the glycoprotein. Glycoproteins that are secreted into the media are relatively easy to purify if serum free media has been used to grow the cells. Glycoproteins that remain trapped in a vesicle (as seen with chicken Thy-1) can be solublized with detergents. Once in detergent, the proteins can be dialyzed against aqueous buffers.

After solublizing the glycoprotein, various chromatographic purification schemes can be used to purify it. In certain embodiments, Lectin Affinity Chromatography can be used. Lectins are non-immune proteins or glycoproteins that bind to specific saccharides and glycoconjugates with high affinity. Because of their binding specificity, lectins show a range of specificities for carbohydrates and glycoconjugates. These lectins can easily be immobilized onto a variety of supports and used for affinity chromatography. Once coupled, lectins are stable with most of the buffers.

Research carried out by Arya, et al., has lead to development of an automated, multi-step, solid-phase strategy for the parallel synthesis of artificial glycopeptide libraries. (Arya, P. et. al., 7 *Med. Chem. Lett.* 1537, 1997, herein expressly incorporated by reference in its entirety). In some embodiments, the specificity exchangers described herein are constructed using this strategy. FIG. 1 illustrates this approach.

Accordingly, different α- or β-carbon linked carbohydrate based aldehyde and carboxylic acid derivatives, protected as acetates (see 18.1 in FIG. 1) can be incorporated either at the N-terminal moiety or at the internal amide nitrogen of short peptides/pseudopeptides (e.g., specificity domains or specificity domains joined to an antigenic domain) in a highly flexible and controlled manner. The chain length of the C-glycoside can be varied and the carbohydrate moiety can be synthesized in either the pyranose or furanose form. Monosaccharides and their derivatives are not the only available carbohydrate building blocks. In certain embodiments, disaccharides and higher order oligosaccharides can also be used as carbohydrate building blocks. C-Glycosides are generally more stable to enzymatic and acid/base hydrolysis than their oxygen counterparts. This method is more versatile than the glycosylated amino acid building block in which the choice of amino acids is limited.

Using this approach, libraries of artificial glycopeptides can be readily synthesized for probing carbohydrate-protein interactions. Several "working models" that display multiple copies of carbohydrates have been developed (see 18.2, 18.3, and 18.4 in FIG. 1) while the dipeptide scaffold may contribute to secondary interactions with the biological target. (Arya, P. et al., 8 *Med. Chem. Lett.* 1127, 1998; Arya, P. et al., 7 *Med. Chem.* 2823, 1999).

Initially, artificial glycopeptides were synthesized by a convergent strategy on a peptide synthesizer. (Kutterer, et.al., 1 *J. Comb. Chem.* 28, 1999). The synthesis of these artificial glycopeptide libraries has been successfully transferred to a fully automated multiple organic synthesizer and each step in the synthesis was optimized. (Arya, P. et al., 2 *Comb. Chem.* 120, 2000). This methodology involves coupling an amino acid to a solid-support resin such as Rink amide MBHA resin or TentaGel derivatized Rink amide resin. After removal of the protecting group on the amino acid, the sugar aldehyde undergoes reductive amination (see 18.3 and 18.4 in FIG. 1) with the resin bound amino group followed by amino acid coupling of the second amino acid. After deprotection of the amino acid, a second reductive amination can occur and/or a sugar acid can be coupled. The sugar moieties are then deacetylated, and the compounds are cleaved from the resin. The synthesis of a 96 compound library can be obtained from just 24 dipeptides and two sugar aldehydes. (See Randell, Karla D., et al., High-throughput Chemistry toward Complex Carbohydrates and Carbohydrate-like Compounds, *National Research Council of Canada*, publication no. 43876, Feb. 13, 2001).

Figure 2:
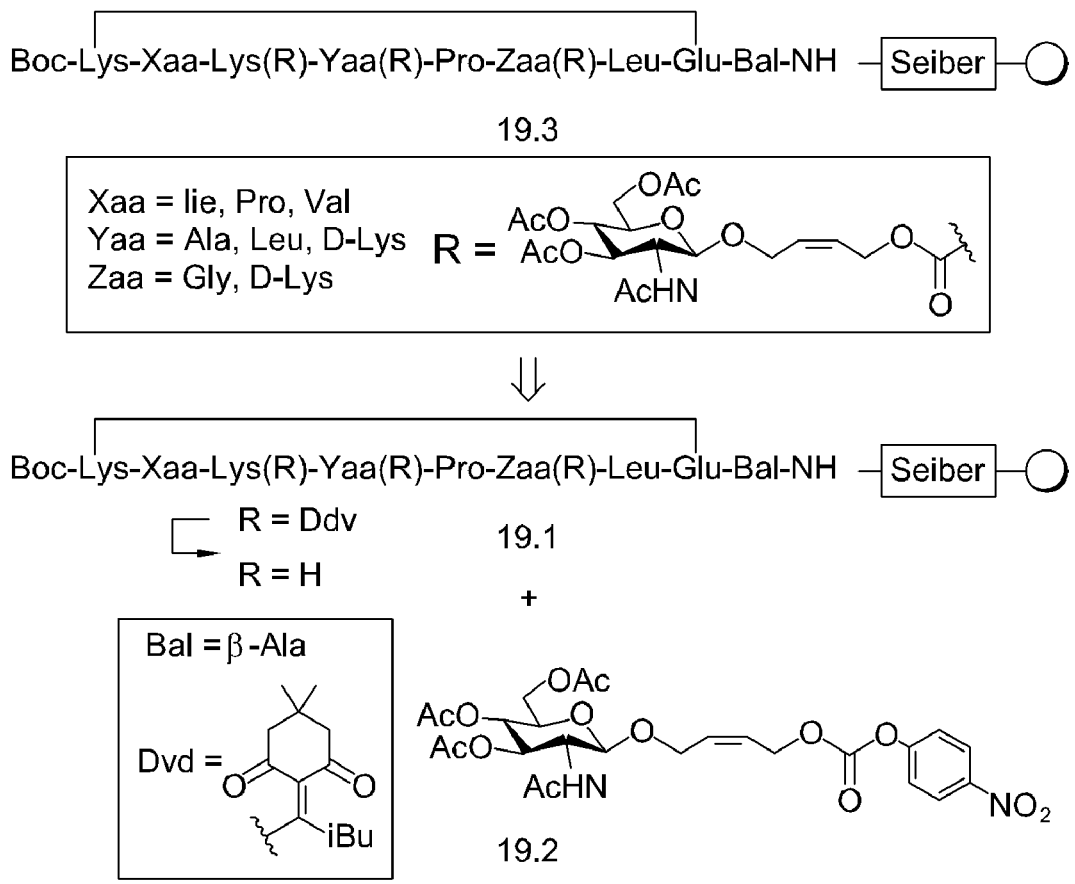
FIG. 2 illustrates a method to artificially synthesize cyclic glycopeptides.
Figure 3:
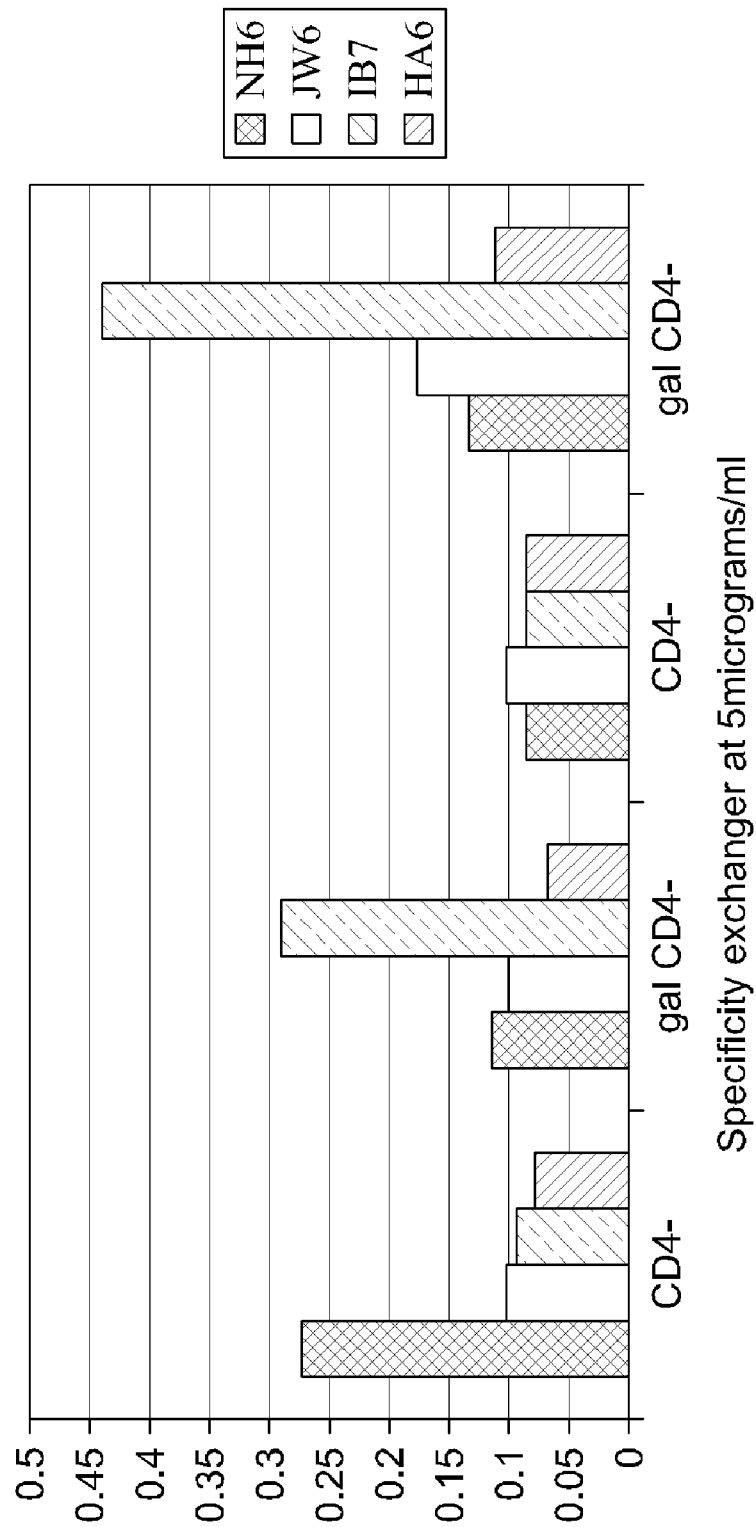
FIG. 3 illustrates the different reactivity of CD4 ligand/receptor specificity exchangers comprising glycosylated (gal-α-1,3 gal-β) or unglycosylated antigenic domains to four different human sera samples. The "X" axis shows the specificity exchangers provided at 5 μg/ml and the "Y" axis shows the OD at 405/650 after detection of antibodies bound.
Figure 4:
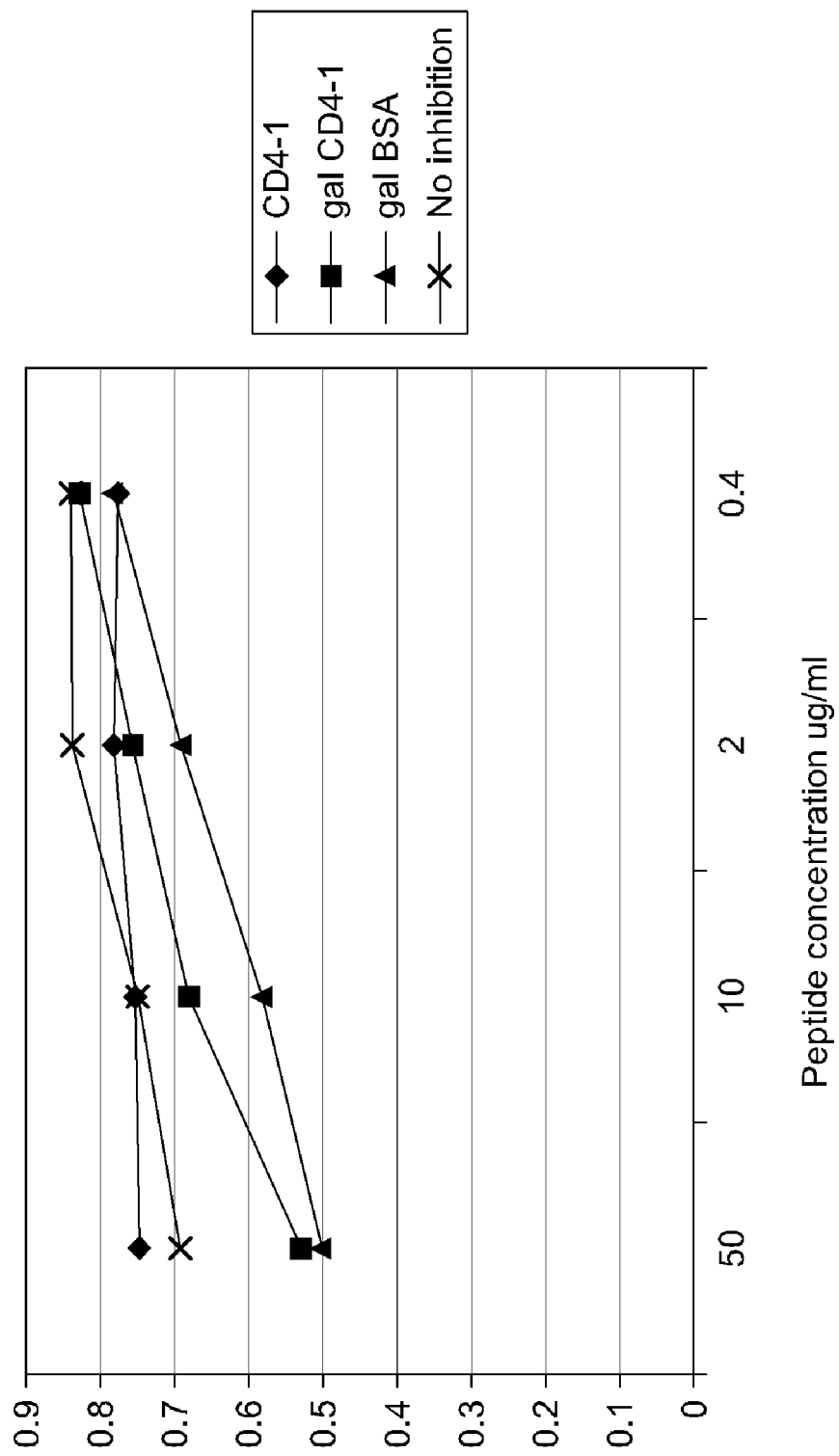
FIG. 4 illustrates the inhibition of binding of CD4 ligand/receptor specificity exchangers comprising glycosylated (gal-α-1,3 gal-β) or unglycosylated antigenic domains in the presence of glycosylated ((gal-α-1,3 gal-β) bovine serum albumin (BSA). The "X" axis shows the concentration of peptide and the "Y" axis shows the OD at 405/650 after detection of antibodies bound.

A recent article describes another approach that can be used to manufacture the specificity exchangers described herein. The synthesis of multivalent cyclic neoglycopeptides has been accomplished. (See Wittmann, V.; Seeberger, et al., 39 *Chem. Int. Ed.* 4348, 2000, herein expressly incorporated by reference in its entirety). A new urethane-type linker based on the Alloc protecting group was developed for the glycosylation reaction, which proceeds virtually quantitatively. A library of cyclic peptides (e.g., specificity exchangers) can be synthesized using the split and mix method on TentaGel resin linked via the Sieber linker. FIG. 2 illustrates this approach.

The synthesis reaction shown in FIG. 2 can be monitored by withdrawal of a small amount of resin from the well and analysis by HPLC in combination with electrospray mass spectrometry. The p-nitrophenyl carbonate derivative of the sugar moiety (see 19.2 in FIG. 2) was attached to three points of the cyclic peptide in one step using a five-fold excess (per attachment point) of the sugar in the presence of DIPEA. A library of eighteen cyclic neoglycopeptides (see 19.3 in FIG. 2) can be efficiently synthesized. This methodology can be applied to the synthesis of many different libraries by varying the distances between the carbohydrate moieties as well as the carbohydrate moiety itself. The section below discusses the incorporation of linkers to the specificity exchangers and/or saccharides or glycoconjugates.

Linkers

In certain embodiments, the saccharide or glycoconjugates can be joined to the specificity exchangers through linkers or by association with a common carrier molecule, as discussed previously. In some embodiments linkers are used to join saccharides to at least one amino acid of the specificity exchangers. In general the term "linkers" refers to elements that promote flexibility of the molecule, reduce steric hindrance, or allow the specificity exchanger to be attached to a support or other molecule. Any suitable linker can be used to attach the saccharide and or glycoconjugate to a specificity exchanger. In certain embodiments the linker can be polyethylene glycol.

Other types of linkers that can be incorporated with a specificity exchanger include avidin or streptavidin (or their ligand—biotin). Through a biotin-avidin/streptavidin linkage, multiple specificity exchangers can be joined together (e.g., through a support, such as a resin, or directly) or individual specificity domains can be joined to a saccharide or glycoconjugate.

Another example of a linker that can be included in a specificity exchanger is referred to as a "λ linker" because it has a sequence that is found on λ phage. Preferred λ sequences are those that correspond to the flexible arms of the phage. These sequences can be included in a specificity exchanger (e.g., between the specificity domain and the saccharide or glycoconjugate or between multimers of the specificity and/or saccharides and glycoconjugates) so as to provide greater flexibility and reduce steric hindrance. The Example below describes the manufacture of a specificity exchanger comprising a plurality of saccharides.

EXAMPLE 1

Two different ligand/receptor specificity exchangers having identical specificity domains (approximately 20 amino acids long) comprising a fragment of the fibrinogen gamma-chain are produced using standard techniques in peptide and glycoconjugate synthesis. The first specificity exchanger (Specificity Exchanger 1) includes an antigenic domain having a peptide obtained from the poliovirus. This poliovirus peptide is recognized by antibodies present in human sera obtained from an individual that had been inoculated against polio. The second specificity exchanger (Specificity Exchanger 2) is identical to Specificity Exchanger 1, except that a saccharide antigen, (e.g., gal-α-1-3 gal) has been added to the specificity exchanger using one of the techniques described above or an another commonly used approach. This gal antigen is also recognized by antibodies present in the human sera obtained from the individual having anti-polio peptide antibodies, described above. Because Specificity Exchangers 1 and 2 have identical specificity domains, which would be expected to bind immobilized ClfA receptor equally well, the ability of the saccharide-containing antigenic domain to recruit more antibodies from human sera than the antigenic domain lacking the gal antigen can be directly analyzed in a sandwich-type plate assay.

Accordingly, serial dilutions of the two ligand/receptor specificity exchangers above are prepared and recombinant ClfA is passively adsorbed at 10 μg/ml to 96 well microtiter plates in 50 mM sodium carbonate buffer, pH 9.6, overnight at 4° C. The diluted ligand/receptor specificity exchangers are then applied to the ClfA-bound plates for 60 minutes at 4° C. with gentle rocking. In some wells, a blocking agent such as BSA is added prior to addition of the specificity exchanger to decrease the non-specific binding. Next, the plates are washed four times with 2 ml of 50 mM sodium carbonate buffer, pH 9.6, to remove any unbound specificity exchanger. After washing, 1 ml of human sera obtained from a subject that has antibodies to both the poliovirus peptide and the gal antigen is added to the wells in 1 ml of 50 mM sodium carbonate buffer, pH 9.6 (i.e., 1:1 ratio), and the plates are rocked gently overnight at 4° C. Again BSA may be included to block non-specific binding. The washing steps performed previously are repeated so as to remove any non-specifically bound antibody.

Several methods of analysis can then be employed. By one approach, the bound antibody is eluted from the specificity exchanger using a typical antibody elution buffer (e.g., Glycine Cl pH 2.5; see Yarmush et al., Biotechnol. Prog. 8:168-178 (1992), hereby expressly incorporated by reference in its entirety) and the absorbance of the eluant is detected spectrophotometrically. In some cases a dye is employed to improve the level of detection. Alternatively, the eluant can be blotted to a membrane (e.g., using a dot blot manifold) and the amount of protein in the eluant can be quantified using silver staining, fluorescence, or a dye-based assay. The eluant can also be applied to a polyacrylamide gel, separated by electrophoresis, and stained or transferred to a membrane, which is then subjected to Western blot using peroxidase labeled antibodies specific for the human immunoglobulins G, A, and M. (peroxidase labeled polyvalent human immunoglobulins available from Sigma). Additionally, the amount of antibody from human sera that bound the specificity exchangers can also be determined in situ (i.e., without eluting from the plate), using typical sandwich-type assays that employ the peroxidase labeled polyvalent antibodies, described above. By these methods of analysis, the plates are developed by incubation with dinitro-phenylene-diamine (Sigma) and the absorbance is analyzed.

It is expected that the analysis described above will confirm that significantly more antibodies from human sera will bind to the antigenic domain composed of the polio peptide and the gal antigen (i.e., Specificity Exchanger 2) than the polio peptide alone (i.e., Specificity Exchanger 1). Because the ClfA receptor is present on pathogens such as *Staphylococcus*, this assay will also confirm that specificity exchangers that comprise the gal antigen (e.g., gal-α-1-3 gal) are more effective at recruiting the natural antibodies present in a subject and, therefore, are more effective at redirecting these antibodies to a pathogen. The next Example describes an approach that was used to synthesize several glycosylated ligand/receptor specificity exchangers.

EXAMPLE 2

Several glycosylated ligand/receptor specificity exchangers (see TABLE 1) comprising a specificity domain corresponding to a CD4 receptor region that interacts with the HIV-1 glycoprotein 120 (see Mizukami T., Fuerst T. R., Berger E. A. & Moss B., *Proc Natl Acad Sci USA*. 85, 9273-7 (1988), herein expressly incorporated by reference in its entirety, were synthesized on solid phase. The peptides were produced in an automatic synthesis robot using Fmoc chemistry (see Ed. Chan W. C. & White P. D. *Fmoc solid phase peptide synthesis-a practical approach* (2000) Oxford university press., herein expressly incorporated by reference in its entirety). Each peptide, still attached to the solid support (resin), was divided in a minor and a major fraction. The minor peptide fractions were cleaved off the resin by treatment with TFA, while the major fractions were left attached to the resin, awaiting glycosylation. The cleaved peptides were analysed by reversed phase HPLC (λ=220 nm) to check the purity. After analysis, the cleaved peptides were lyophilised.

A reagent including the sugar Gal-α1-3Gal has been shown to absorb human anti-Gal-α1-3Gal antibodies (Rieben R., von Allmen E., Korchagina E. Yu. Et al. *Xenotransplantation.* 2, 98-106 (1995), herein expressly incorporated by reference in its entirety). The formula for Gal-α1-3Gal-β is provided below as Formula 1.

Formula 1:

1

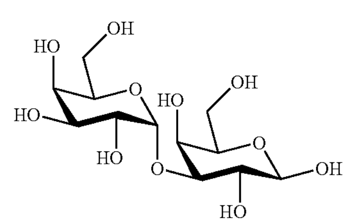

The sugar reagent (Galα1-3Galβ1-O(CH$_2$)$_3$NH$_2$ (Lectinity corp., product no. 88)) was coupled to the side chain of an aspartic acid (Formula 2):

Formula 2:

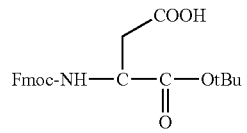

(Novabiochem, product no. 04-12-1080)

The amino acid was protected both at the N-terminal and C-terminal ends. A covalent bond between the sugar amino group and the amino acid carboxyl group, was formed. (See Synthesis 1).

Synthesis 1:

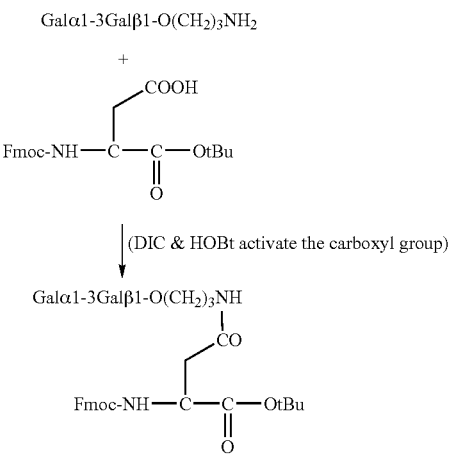

The coupling reaction was monitored by analysing samples from the reaction mixture by reversed phase HPLC using λ=266 nm since the Fmoc protecting group absorbs UV light strongly at this wavelength. The coupling reaction was stopped after ~4-6 h. The glyco-amino acid was purified by reversed phase HPLC (λ=266 nm). The purified glyco-amino acid was lyophilised.

Next, deprotection of the glyco-amino acid was performed. To allow coupling of the glyco-amino acid to the CD4 peptides, the OtBu-protecting group was cleaved off the glyco-amino acid C-terminus, by treatment with TFA (see Synthesis 2).

Synthesis 2:

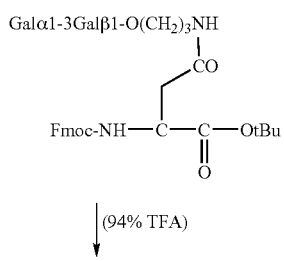

-continued

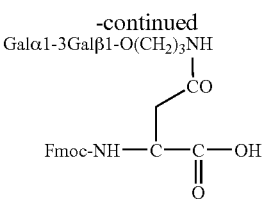

The deprotection was monitored by reversed phase HPLC (λ=266 nm). After ~2 h, the deprotection was stopped. Most of the TFA was evaporated by nitrogen gas. The remaining solution was diluted 1/10 with water. The deprotected glyco-amino acid was purified by reversed phase HPLC (λ=266 nm). The purified and deprotected glyco-amino acid was lyophilised.

Following deprotection of the glyco-amino acid, coupling to the CD4 and CDR specificity domain peptides was performed. The glyco-amino acid was covalently linked to the N-terminal ends of the resin-bound specificity domains using Fmoc chemistry (see Synthesis 3). The coupling reaction was stopped after ~6 h.

Synthesis 3:

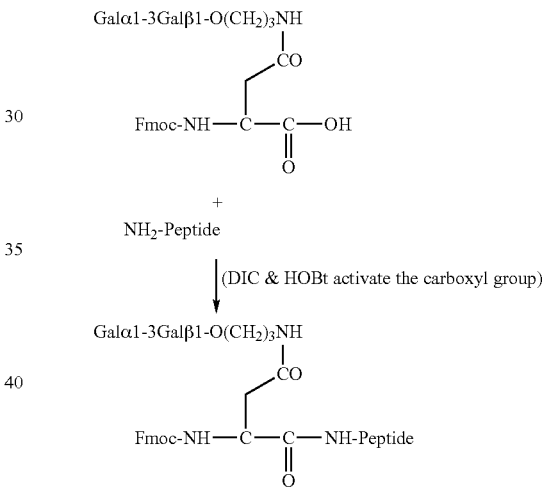

The glycosylated specificity exchangers were deprotected and cleaved off their solid supports by treatment with TFA. The cleaved glycosylated specificity exchangers were analysed by reversed phase HPLC (λ=220 nm) to check the purity in comparison with the corresponding non-glycosylated peptides. Glycosylation-specific peaks were purified by reversed phase HPLC (λ=220 nm). The purified glycosylated specificity exchangers were lyophilised. After lyophilization, a fraction of each glycosylated specificity exchangere was analysed by MALDI-MS to verify its identity. The following Example describes several cellular-based characterization assays that can be performed to determine whether a ligand/receptor specificity exchanger inhibits the proliferation of a pathogen.

EXAMPLE 3

One type of pathogen-based characterization assay involves the binding of ligand/receptor specificity exchangers to bacteria disposed on a support. As in Example 1, separate assays are performed to compare the binding affinities of Specificity Exchangers 1 and 2. Bacteria that produce ClfA (e.g., *Staphylococcus aureus*, or *Escherichia coli.*) are grown in culture or on several agar plates in a suitable growth media (e.g., LB broth, blood broth, LB agar or blood agar). The cells are grown to confluency so as to produce a solid bacterial lawn. Next, several dilutions of Specificity Exchanger 1 and Specificity Exchanger 2 are added to separate plates. For example, different plates receive 500 mg, 1 mg, 5 mg, 10 mg, 25 mg, and 50 mg of either Specificity Exchanger 1 or 2 in a total volume of 200 μl of PBS. The plates are incubated at 37° C. for at least 4 hours.

Subsequently, the non-bound ligand/receptor specificity exchangers are removed with successive washes with PBS (e.g., 3 washes with 2 ml of PBS per wash). Next, serial dilutions of the human sera used in Example 1 (i.e., it contains antibodies to both the polio peptide and the gal antigen) are added to the plates (e.g., 1:100-1:1000 dilutions of human sera are provided). After a 60 minute incubation, the plates are washed with PBS (e.g., 3 washes with 2 ml of PBS per wash) to remove unbound primary antibody. The bacterial proteins, specificity exchangers, and human antibodies are then transferred to a membrane. Appropriate controls include the membrane itself, bacterial proteins transferred to the membrane without a ligand/receptor specificity exchanger but containing antibodies from human sera, and bacterial proteins transferred to the membrane with ligand/receptor specificity exchanger but no antibodies from human sera.

The amount of antibodies redirected to the bacteria can then be ascertained by using the peroxidase labeled antibodies specific for the human immunoglobulins G, A, and M, as described in Example 1. An appropriate dilution of the secondary antibody is contacted with the membrane for 60 minutes and the non-bound secondary antibody is washed from the membrane with PBS (e.g., 3 washes with 2 ml of PBS per wash). The bound secondary antibody is then detected by incubating the membrane with dinitro-phenylene-diamine (Sigma).

The data will show that the specificity exchanger comprising the gal antigen (Specificity Exchanger 2) redirected antibodies present in human sera to the bacterial pathogen more efficiently than Specificity Exchanger 1. This example also demonstrates that specificity exchangers that comprise a plurality of saccharides or glycoconjugates (e.g., gal-α-1-3 gal) will be more effective at redirecting antibodies present in a subject to a pathogen in vivo. The next Example describes a pathogen-based characterization assay that was performed to evaluate the ability of glycosylated ligand/receptor specificity exchangers to interact with HIV.

EXAMPLE 4

Glycosylated ligand/receptor specificity exchangers specific for HIV were produced according to the approaches described in Example 2. To evaluate the ability of glycosylated specificity exchangers to bind human Gal-alpha1,3-Gal-specific antibodies, glycosylated and non-glycosylated versions of the same ligand/receptor specificity exchanger were coated on solid phase of microtitre plates. Four human sera were allowed to bind to the coated peptides, and an enzyme labeled anti-human antibody indicated bound human antibodies. The results showed that only the glycosylated peptides were able to bind human antibodies (human sera IB72; FIG. 3).

To further evaluate the ability of the glycosylated specificity exchangers to bind to a pathogen, a glycosylated peptide competitive assay was performed using the most reactive human sera (IB72). In brief, Gal-alpha1,3-Gal-labeled bovine serum albumin (Gal-BSA) was coated onto 96-well microplates in sodium carbonate buffer (pH: 9.6) at +4° C. overnight. Dilutions of human sera and dilutions of glycopeptides (glycosylated HIV-specific ligand/receptor specificity exchangers or Gal-BSA) or non-glycosylated peptides (HIV-specific ligand/receptor specificity exchangers or BSA) were preincubated in phosphate-buffered saline (PBS) containing 1% bovine albumin, 2% goat serum and 0.05% Tween 20 at 37° C. for 1 h. The mixture was then added to the coated plates and incubated at 37° C. for 1 h, then washed 3 times with phosphate-buffered saline (PBS) containing 0.05% Tween 20 (pH: 7.4).

Bound antibodies were indicated with goat anti-human polyvalent Ig, conjugated with alkaline phosphatase. The plates were incubated and washed as described above. Plates were developed with phosphatase substrate at room temperature for 30 min, stopped with 1 M NaOH. Optical density (OD) at 405 nm/650 nm was determined to quantify the inhibition. The results are provided in FIG. 4, which shows that the human antibody binding to Gal-BSA could only be inhibited by either Gal-BSA or the glycosylated peptide. Thus, specificity exchangers that bind Gal-alpha1,3-Gal-specific antibodies had been generated. Gal-BSA mixed with human sera in the same conditions as mentioned above was used as positive control and 100% inhibition was observed.

The following example will demonstrate that specificity exchangers comprising a plurality of saccharides or glycoconjugates (e.g., gal-α-1-3 gal) are more effective at redirecting antibodies present in a subject to a pathogen in vivo.

EXAMPLE 5

There are many animal models that are suitable for evaluating the ability of a ligand/receptor specificity exchanger to inhibit pathogenic infection. Mice are preferred because they are easy to maintain and are susceptible to bacterial infection, viral infection, and cancer. Chimpanzees are also preferred because of their close genetic relationship to humans.

To test the ability of a ligand/receptor specificity exchanger to treat a bacterial infection in mice, the following characterization assay can be performed. Several female CF-1 outbred mice (Charles Rivers Laboratories) of approximately 8 weeks of age and 25 gram body mass are inoculated intraperitoneally with overnight cultures of *Staphylococcus aureus*. Blood samples are drawn from the mice and tests are conducted to verify that *Staphylococcus aureus* is present in the subjects.

The infected mice are injected with a suitable amount of either Specificity Exchanger 1 or 2, as described in Examples 1 and 2. A small sample (e.g., 0.5 mL) of the human serum used in Examples 1 and 2 is also injected into the infected mice. For various time points after the injection of the human serum for up to two weeks, the mice are monitored for the presence and prevalence of *Staphylococcus aureus*. The progress or decline in *Staphylococcus aureus* infection is plotted.

The data will show that Specificity Exchanger 2 more efficiently inhibited the proliferation of *Staphylococcus aureus* than Specificity Exchanger 1, verifying that the presence of the gal antigen was more efficient at redirecting the human antibodies present in the subject to the pathogen. The section below describes several pharmaceuticals comprising specificity exchangers that comprise saccharides and/or glycoconjugates.

Pharmaceuticals Comprising Specificity Exchangers that Comprise Saccharides and/or Glycoconjugates The specificity exchangers described herein are suitable for incorporation into pharmaceuticals for administration to subjects in need of a compound that treats or prevents infection by a pathogen. These pharmacologically active compounds can be processed in accordance with conventional methods of galenic pharmacy to produce medicinal agents for administration to mammals including humans. The active ingredients can be incorporated into a pharmaceutical product with and without modification. Further, the manufacture of pharmaceuticals or therapeutic agents that deliver the pharmacologically active compounds of this invention by several routes are aspects of the present invention. For example, and not by way of limitation, DNA, RNA, and viral vectors having sequences encoding a specificity exchanger described herein are used with embodiments of the invention. Nucleic acids encoding the embodied specificity exchangers can be administered alone or in combination with other active ingredients.

The specificity exchangers can be employed in admixture with conventional excipients, i.e., pharmaceutically acceptable organic or inorganic carrier substances suitable for parenteral, enteral (e.g., oral) or topical application that do not deleteriously react with the pharmacologically active ingredients described herein. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more vehicles that can be used are described in Remmington's Pharmaceutical Sciences, 15th Edition, Easton:Mack Publishing Company, pages 1405-1412 and 1461-1487(1975) and The National *Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like so long as the auxiliary agents does not deleteriously react with the specificity exchangers.

The effective dose and method of administration of a particular pharmaceutical having a specificity exchanger that comprises a plurality of saccharides and/or glycoconjugates can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). For example, the effective dose of a specificity exchanger can be evaluated using the characterization assays described above. The data obtained from these assays is then used in formulating a range of dosage for use with other organisms, including humans. The dosage of such compounds lies preferably within a range of circulating concentrations that include the ED50 with no toxicity. The dosage varies within this range depending upon type of specificity exchanger, the dosage form employed, sensitivity of the organism, and the route of administration.

Normal dosage amounts of a specificity exchanger can vary from approximately 1 to 100,000 micrograms, up to a total dose of about 10 grams, depending upon the route of administration. Desirable dosages include about 250 mg-1 mg, about 50 mg-200 mg, and about 250 mg-500 mg.

In some embodiments, the dose of a specificity exchanger preferably produces a tissue or blood concentration or both from approximately 0.1 μM to 500 μM. Desirable doses produce a tissue or blood concentration or both of about 1 to 800 μM. Preferable doses produce a tissue or blood concentration of greater than about 10 μM to about 500 μM. Although doses that produce a tissue concentration of greater than 800 μM are not preferred, they can be used. A constant infusion of a specificity exchanger can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism being treated, and weight or size of the organism, diet, time and frequency of administration, drug combination(s), reaction sensitivities, and tolerance/response to therapy. Short acting pharmaceutical compositions are administered daily or more frequently whereas long acting pharmaceutical compositions are administered every 2 or more days, once a week, or once every two weeks or even less frequently.

Routes of administration of the pharmaceuticals include, but are not limited to, topical, transdermal, parenteral, gastrointestinal, transbronchial, and transalveolar. Transdermal administration is accomplished by application of a cream, rinse, gel, etc. capable of allowing the specificity exchangers to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the specificity exchangers described herein that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein expressly incorporated by reference in its entirety.

Compositions having the specificity exchangers described herein that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having the specificity exchangers described herein that are suitable for transbronchial and transalveolar administration include, but are not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the specificity exchangers described herein.

Compositions having the specificity exchangers described herein that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the specificity exchanger has been obtained, it can be administered to an organism in need to treat or prevent pathogenic infection.

Aspects of the invention also include a coating for medical equipment such as prosthetics, implants, and instruments. Coatings suitable for use on medical devices can be provided by a gel or powder containing the specificity exchanger or by a polymeric coating into which a specificity exchanger is suspended. Suitable polymeric materials for coatings of devices are those that are physiologically acceptable and through which a therapeutically effective amount of the specificity exchanger can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, herein expressly incorporated by reference in its entirety. The section below describes methods of treating and preventing disease using the specificity exchangers described herein.

Treatment and Prevention of Disease Using a Specificity Exchanger that Comprises a Plurality of Saccharides and/or a Glycoconjugate Pharmaceuticals comprising the specificity exchangers described herein can be administered to a subject in need to treat and/or prevent infection by a pathogen that has a receptor. Such subjects in need can include individuals at risk of contacting a pathogen or individuals who are already infected by a pathogen. These individuals can be identified by standard clinical or diagnostic techniques.

By one approach, for example, a subject suffering from a bacterial infection is identified as a subject in need of an agent that inhibits proliferation of a pathogen. This subject is then provided a therapeutically effective amount of a specificity exchanger described herein. The specificity exchanger used in this method comprises a specificity domain that interacts with a receptor present on the bacteria (e.g., extracellular fibrinogen binding protein (Efb), collagen binding protein, vitronectin binding protein, laminin binding protein, plasminogen binding protein, thrombospondin binding protein, clumping factor A (ClfA), clumping factor B (ClfB), fibronectin binding protein, coagulase, and extracellular adherence protein). The specificity exchanger also comprises an antigenic domain that has a plurality of saccharides and/or glycoconjugates, which are recognized by high titer antibodies present in the subject in need. It may also be desired to screen the subject in need for the presence of high titer antibodies that recognize the antigenic domain prior to providing the subject the specificity exchanger. This screening can be accomplished by EIA or ELISA using immobilized antigenic domain or specificity exchanger, as described above.

Similarly, a subject in need of an agent that inhibits viral infection can be administered a specificity exchanger that recognizes a receptor present on the particular etiologic agent. Accordingly, a subject in need of an agent that inhibits viral infection is identified by standard clinical or diagnostic procedures. Next, the subject in need is provided a therapeutically effective amount of a specificity exchanger that interacts with a receptor present on the type of virus infecting the individual. As above, it may be desired to determine whether the subject has a sufficient titer of antibody to interact with the antigenic domain of the specificity exchanger prior to administering the specificity exchanger.

In the same vein, a subject in need of an agent that inhibits the proliferation of cancer can be administered a specificity exchanger that interacts with a receptor present on the cancer cell. For example, a subject in need of an agent that inhibits proliferation of cancer is identified by standard clinical or diagnostic procedures; then the subject in need is provided a therapeutically effective amount of a specificity exchanger that interacts with a receptor present on the cancer cells infecting the subject. As noted above, it may be desired to determine whether the subject has a sufficient titer of antibody to interact with the antigenic domain of the specificity exchanger prior to administering the specificity exchanger.

The specificity exchangers described herein can also be administered to subjects as a prophylactic to prevent the onset of disease. Virtually anyone can be administered a specificity exchanger described herein for prophylactic purposes, (e.g., to prevent a bacterial infection, viral infection, or cancer). It is desired, however, that subjects at a high risk of contracting a particular disease are identified and provided a specificity exchanger. Subjects at high risk of contracting a disease include individuals with a family history of disease, the elderly or the young, or individuals that come in frequent contact with a pathogen (e.g., health care practitioners). Accordingly, subjects at risk of becoming infected by a pathogen that has a receptor are identified and then are provided a prophylactically effective amount of specificity exchanger.

One prophylactic application for the specificity exchangers described herein concerns coating or cross-linking the specificity exchanger to a medical device or implant. Implantable medical devices tend to serve as foci for infection by a number of bacterial species. Such device-associated infections are promoted by the tendency of these organisms to adhere to and colonize the surface of the device. Consequently, there is a considerable need to develop surfaces that are less prone to promote the adverse biological reactions that typically accompany the implantation of a medical device.

By one approach, the medical device is coated in a solution of containing a specificity exchanger. Prior to implantation, medical devices (e.g., a prosthetic valve) can be stored in a solution of specificity exchangers, for example. Medical devices can also be coated in a powder or gel having a specificity exchanger. For example, gloves, condoms, and intrauterine devices can be coated in a powder or gel that contains a specificity exchanger that interacts with a bacterial or viral receptor. Once implanted in the body, these specificity exchangers provide a prophylactic barrier to infection by a pathogen.

In some embodiments, the specificity exchanger is immobilized to the medical device. As described above, the medical device is a support to which a specificity exchanger can be attached. Immobilization may occur by hydrophobic interaction between the specificity exchanger and the medical device but a preferable way to immobilize a specificity exchanger to a medical device involves covalent attachment. For example, medical devices can be manufactured with a reactive group that interacts with a reactive group present on the specificity exchanger.

By one approach, a periodate is combined with a specificity exchanger comprising a 2-aminoalcohol moiety to form an aldehyde-functional exchanger in an aqueous solution having a pH between about 4 and about 9 and a temperature between about 0 and about 50 degrees Celsius. Next, the aldehyde-functional exchanger is combined with the biomaterial surface of a medical device that comprises a primary amine moiety to immobilize the specificity exchanger on the support surface through an imine moiety. Then, the imine moiety is reacted with a reducing agent to form an immobilized specificity exchanger on the biomaterial surface through a secondary amine linkage. A similar chemistry can be used to attach the sugar to the support and/or specificity domain of the specificity exchanger, as well. Other approaches for cross-linking molecules to medical devices, (such as described in U.S. Pat. No. 6,017,741, herein expressly incorporated by reference in its entirety), can be modified to immobilize the specificity exchangers described herein.

Although the invention has been described with reference to embodiments and examples, it should be understood that various modifications can be made without departing from the spirit of the invention. Accordingly, the invention is limited only by the following claims. All references cited herein are hereby expressly incorporated by reference in their entireties.

What is claimed is:

1. A method of binding an anti-gal antibody to a cancer cell present in a subject comprising:
    providing an isolated glycoconjugate to a subject that has an anti-gal antibody, wherein said isolated glycoconjugate comprises:
        a first domain that is a ligand for a receptor on the cancer cell present in said subject or an amino acid sequence of an antibody that binds the cancer cell present in said subject; and
        a second domain that has at least one Gal α(1,3)Gal saccharide synthetically conjugated to said ligand or said amino acid sequence of an antibody, wherein said at least one Gal α(1,3)Gal saccharide is directly joined to the first domain at one amino acid, such that said first domain binds to said cancer cell and said second domain binds to said anti-gal antibody, thereby generating a complex in said subject that comprises said anti-gal antibody, said glycoconjugate, and said cancer cell.

2. The method according to claim 1, wherein the glycoconjugate comprises a ligand for a receptor on the cancer cell.

3. The method according to claim 1, wherein the glycoconjugate comprises an amino acid sequence of an antibody that binds the cancer cell.

4. The method according to claim 3, wherein the amino acid sequence encodes a complementarity determining region (CDR) of the antibody.

5. The method according to claim 1, wherein the first domain is between 3-200 amino acids in length.

6. The method according to claim 1, wherein the first domain is between 5-100 amino acids in length.

7. The method according to claim 1, wherein the first domain is between 8-50 amino acids in length.

8. The method according to claim 1, wherein the first domain is between 10-25 amino acids in length.

9. The method according to claim 1, wherein said at least one Gal α(1,3)Gal saccharide is directly joined to the first domain at a hydroxylated amino acid.

10. The method according to claim 1, wherein a plurality of Gal α(1,3)Gal saccharides are joined to the first domain.

11. The method according to claim 1, wherein said glycoconjugate further comprises a peptide sequence that is recognized as non-self by existing antibodies in the subject.

12. A method of generating a complex that comprises an anti-gal antibody, an isolated glycoconjugate, and a cancer cell in a subject comprising:
    (i) identifying a subject that has a cancer cell and an anti-gal antibody;
    (ii) providing to said subject an isolated glycoconjugate that comprises:
        a first domain that is a ligand for a receptor on the cancer cell or an amino acid sequence of an antibody that binds the cancer cell; and
        a second domain that has at least one Gal α(1,3)Gal saccharide synthetically conjugated to said ligand or said amino acid sequence of an antibody, wherein said at least one Gal α(1,3)Gal saccharide is directly joined to the first domain at one amino acid, such that said first domain binds to said cancer cell and said second domain binds to said anti-gal antibody, thereby generating a complex that comprises said anti-gal antibody, said glycoconjugate, and said cancer cell.

13. The method according to claim 12, wherein said at least one Gal α(1,3)Gal saccharide is directly joined to the first domain at a hydroxylated amino acid.

14. A method for forming a complex, comprising:
    (i) administering to a subject a bifunctional binding moiety comprising a first domain that is a ligand for a receptor on a cancer cell or an amino acid sequence of an antibody that binds a cancer cell and a second domain that has at least one Gal α(1,3)Gal saccharide synthetically conjugated to said ligand or said amino acid sequence of an antibody, wherein said at least one Gal α(1,3)Gal saccharide is directly joined to the first domain at one amino acid;

(ii) binding said first domain to a cancer cell in the subject; and
(iii) binding said second domain to anti-gal antibody in the subject, thereby forming said complex.

15. The method according to claim 14, wherein said at least one Gal α(1,3)Gal saccharide is directly joined to the first domain at a hydroxylated amino acid.

16. The method according to claim 1, wherein the glycoconjugate is a peptide.

17. The method according to claim 12, wherein the glycoconjugate comprises a ligand for a receptor on the cancer cell.

18. The method according to claim 12, wherein the glycoconjugate comprises an amino acid sequence of an antibody that binds the cancer cell.

19. The method according to claim 18, wherein the amino acid sequence encodes a complementarity determining region (CDR) of the antibody.

20. The method according to claim 12, wherein the first domain is between 3-200 amino acids in length.

21. The method according to claim 12, wherein the first domain is between 5-100 amino acids in length.

22. The method according to claim 12, wherein the first domain is between 8-50 amino acids in length.

23. The method according to claim 12, wherein the first domain is between 10-25 amino acids in length.

24. The method according to claim 12, wherein a plurality of Gal α(1,3)Gal saccharides are joined to the first domain.

25. The method according to claim 12, wherein said glycoconjugate further comprises a peptide sequence that is recognized as non-self by existing antibodies in the subject.

26. The method according to claim 12, wherein the glycoconjugate is a peptide.

27. The method according to claim 14, wherein the bifunctional binding moiety comprises a ligand for a receptor on a cancer cell.

28. The method according to claim 14, wherein the bifunctional binding moiety comprises an amino acid sequence of an antibody that binds a cancer cell.

29. The method according to claim 28, wherein the amino acid sequence encodes a complementarity determining region (CDR) of the antibody.

30. The method according to claim 14, wherein the first domain is between 3-200 amino acids in length.

31. The method according to claim 14, wherein the first domain is between 5-100 amino acids in length.

32. The method according to claim 14, wherein the first domain is between 8-50 amino acids in length.

33. The method according to claim 14, wherein the first domain is between 10-25 amino acids in length.

34. The method according to claim 14, wherein a plurality of Gal α(1,3)Gal saccharides are joined to the first domain.

35. The method according to claim 14, wherein said bifunctional binding moiety further comprises a peptide sequence that is recognized as non-self by existing antibodies in the subject.

36. The method according to claim 14, wherein the bifunctional binding moiety is a peptide.

* * * * *

SEQUENCE LISTING

```
<160> NUMBER OF SEQ ID NOS: 9

<210> SEQ ID NO 1
<211> LENGTH: 17
<212> TYPE: PRT
<213> ORGANISM: Homo sapiens

<400> SEQUENCE: 1

Asp Cys Asp Leu Ile Tyr Tyr Asp Tyr Glu Glu Asp Tyr Tyr Phe Asp
1               5                   10                  15

Tyr

<210> SEQ ID NO 2
<211> LENGTH: 16
<212> TYPE: PRT
<213> ORGANISM: Homo sapiens

<400> SEQUENCE: 2

Asp Gln Phe His Trp Lys Asn Ser Asn Gln Ile Lys Ile Leu Gly Asn
1               5                   10                  15

<210> SEQ ID NO 3
<211> LENGTH: 16
<212> TYPE: PRT
<213> ORGANISM: Homo sapiens

<400> SEQUENCE: 3

Asp Gln Gly Ser Phe Leu Thr Lys Gly Pro Ser Lys Leu Asn Asp Arg
1               5                   10                  15

<210> SEQ ID NO 4
<211> LENGTH: 15
<212> TYPE: PRT
<213> ORGANISM: Homo sapiens

<400> SEQUENCE: 4

Gln Phe His Trp Lys Asn Ser Asn Gln Ile Lys Ile Leu Gly Asn
1               5                   10                  15

<210> SEQ ID NO 5
<211> LENGTH: 15
<212> TYPE: PRT
<213> ORGANISM: Homo sapiens

<400> SEQUENCE: 5

Asn Ser Asn Gln Ile Lys Ile Leu Gly Asn Gln Gly Ser Phe Leu
1               5                   10                  15

<210> SEQ ID NO 6
<211> LENGTH: 15
<212> TYPE: PRT
<213> ORGANISM: Homo sapiens

<400> SEQUENCE: 6

Lys Ile Leu Gly Asn Gln Gly Ser Phe Leu Thr Lys Gly Pro Ser
1               5                   10                  15
```

```
<210> SEQ ID NO 7
<211> LENGTH: 15
<212> TYPE: PRT
<213> ORGANISM: Homo sapiens

<400> SEQUENCE: 7

Gln Gly Ser Phe Leu Thr Lys Gly Pro Ser Lys Leu Asn Asp Arg
1               5                   10                  15

<210> SEQ ID NO 8
<211> LENGTH: 15
<212> TYPE: PRT
<213> ORGANISM: Homo sapiens

<400> SEQUENCE: 8

Thr Lys Gly Pro Ser Lys Leu Asn Asp Arg Ala Asp Ser Arg Arg
1               5                   10                  15

<210> SEQ ID NO 9
<211> LENGTH: 15
<212> TYPE: PRT
<213> ORGANISM: Homo sapiens

<400> SEQUENCE: 9

Lys Leu Asn Asp Arg Ala Asp Ser Arg Arg Ser Leu Trp Asp Gln
1               5                   10                  15
```